(12) United States Patent
Pfeiffer

(10) Patent No.: US 11,865,032 B2
(45) Date of Patent: Jan. 9, 2024

(54) DEVICE FOR ALLEVIATING DYSPAREUNIA

(71) Applicant: JSP Innovations LLC, Decatur, IL (US)

(72) Inventor: Jeffrey S. Pfeiffer, Decatur, IL (US)

(73) Assignee: JSP Innovations LLC, Decatur, IL (US)

( * ) Notice: Subject to any disclaimer, the term of this patent is extended or adjusted under 35 U.S.C. 154(b) by 643 days.

(21) Appl. No.: 16/952,012

(22) Filed: Nov. 18, 2020

(65) Prior Publication Data

US 2021/0145631 A1 May 20, 2021

Related U.S. Application Data

(60) Provisional application No. 62/937,013, filed on Nov. 18, 2019.

(51) Int. Cl.
*A61F 6/08* (2006.01)
*A61H 19/00* (2006.01)

(52) U.S. Cl.
CPC ..................... *A61F 6/08* (2013.01)

(58) Field of Classification Search
CPC .. A61F 6/08; A61F 6/14; A61H 19/32; A61H 19/40; A61H 19/44; A61H 19/50
See application file for complete search history.

(56) References Cited

U.S. PATENT DOCUMENTS

| | | | | |
|---|---|---|---|---|
| 3,646,929 A * | 3/1972 | Bonnar | ............... | A61F 2/005 606/119 |
| 4,393,871 A * | 7/1983 | Vorhauer | ............... | A61K 9/0036 521/905 |
| 4,401,534 A * | 8/1983 | Goepp | ............... | A61F 6/08 264/222 |
| 5,609,559 A * | 3/1997 | Weitzner | ............... | A61F 2/005 600/29 |
| 5,771,899 A * | 6/1998 | Martelly | ............... | A61F 6/08 128/830 |
| 6,770,025 B2 * | 8/2004 | Zunker | ............... | A61F 2/005 600/29 |
| 10,111,737 B2 * | 10/2018 | Leyendecker | ............... | A61F 2/005 |
| 2007/0089750 A1 * | 4/2007 | Astani | ............... | A61F 2/005 128/830 |
| 2010/0154801 A1 * | 6/2010 | Carey | ............... | A61F 2/005 128/834 |
| 2013/0025604 A1 * | 1/2013 | Harmanli | ............... | A61F 6/08 128/834 |

(Continued)

OTHER PUBLICATIONS

Pfeiffer, Jeffery May 27, 2021, WO 2021/102054 A2.*

*Primary Examiner* — Camtu T Nguyen
(74) *Attorney, Agent, or Firm* — Leydig, Voit & Mayer, Ltd.

(57) ABSTRACT

A device for alleviating dyspareunia comprises a pliable body filled with a resilient and soft material, such as, medical grade silicone, for example. The body, which can be a rounded shape, including ovoid or annular, can be configured to act as a buffer or shock absorber for the upper vagina and cervix during intercourse. The resilient nature of the pliable body allows forces to be displaced laterally instead of cephalad, to thereby help alleviate pain by relieving pressure on the cervix, cardinal and uterosacral ligaments, vaginal apex, etc.

20 Claims, 36 Drawing Sheets

(56) References Cited

U.S. PATENT DOCUMENTS

| | | | |
|---|---|---|---|
| 2013/0276792 A1* | 10/2013 | Moch | A61F 6/146 |
| | | | 264/328.1 |
| 2016/0008215 A1* | 1/2016 | Pfeiffer | A61H 23/02 |
| | | | 600/38 |

\* cited by examiner 10   20   30

Step 710

Step 720

Step 730

Step 740

Step 750

Step 760

Step 770

Step 780

Step 790

Step 810

Step 820

Step 830

Step 840

Step 850

Step 860

Step 870

Step 880

Step 890

DEVICE FOR ALLEVIATING DYSPAREUNIA

CROSS-REFERENCE TO RELATED APPLICATIONS

This patent application claims the benefit of priority to U.S. Provisional Patent Application No. 62/937,013, filed Nov. 18, 2019, and entitled, "Device for Alleviating Dyspareunia," which is incorporated in its entirety herein by this reference.

TECHNICAL FIELD

This patent disclosure relates generally to a sexual enhancement device and, more particularly, to a sexual enhancement device configured to help alleviate dyspareunia.

BACKGROUND

Dyspareunia, i.e., pain during intercourse, is very common with as many as nearly three out of four women experiencing dyspareunia at some point in their lives. For some women, pain is only a temporary problem, but for others it is a long-term issue. There are a number of reasons women experience pain during sex. It may be a gynecological problem, such as ovarian cysts or endometriosis, or it may be caused by problems with sexual response, such as lack of desire or arousal.

It is also variable where women feel pain during intercourse. They may experience pain in the vulva, vagina, perineum, lower back, pelvic region, uterus, or bladder. Another common type of dyspareunia is deep or collision pain. This occurs when the penis comes into contact or bumps into the cervix or vaginal cuff. The average vagina is approximately four inches long, but it doubles in length during arousal or excitation to approximately eight inches long. During sex that involves deeper penetration, collision dyspareunia can be very common and painful.

There is a continued need in the art to provide additional solutions to enhance sexual intercourse. For example, there is a continued need for techniques for alleviating dyspareunia.

It will be appreciated that this background description has been created by the inventor to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

SUMMARY

The present disclosure, in one aspect, is directed to embodiments of a device for alleviating dyspareunia. In one embodiment, a device for alleviating dyspareunia includes a body and a strap. The body includes an outer skin and a core disposed within the outer skin. The strap is connected to the body.

The outer skin of the body is made from a first composition including a first material, and the core of the body is made from a second composition comprising a second material. The first composition is harder than the second composition. The outer skin and the core are configured such that the body has a modulus of elasticity in a range between 5 kPa and 10 kPa.

In another embodiment, a device for alleviating dyspareunia includes a body having an outer skin and an inner core disposed within the outer skin. The outer skin is made from a first composition including a first material, and the inner core is made from a second composition comprising a second material. The first composition is harder than the second composition. The outer skin and the core are configured such that the body has a modulus of elasticity in a range between 5 kPa and 10 kPa. The body is annular and defines a central hole configured to accommodate at least one finger therethrough for providing a grasping point for use during removal of the device from a user's vagina.

Further and alternative aspects and features of the disclosed principles will be appreciated from the following detailed description and the accompanying drawings. As will be appreciated, the device for alleviating dyspareunia disclosed herein is capable of being carried out in other and different embodiments, and capable of being modified in various respects. Accordingly, it is to be understood that both the foregoing general description and the following detailed description are exemplary and explanatory only and do not restrict the scope of the appended claims.

Figure 1:
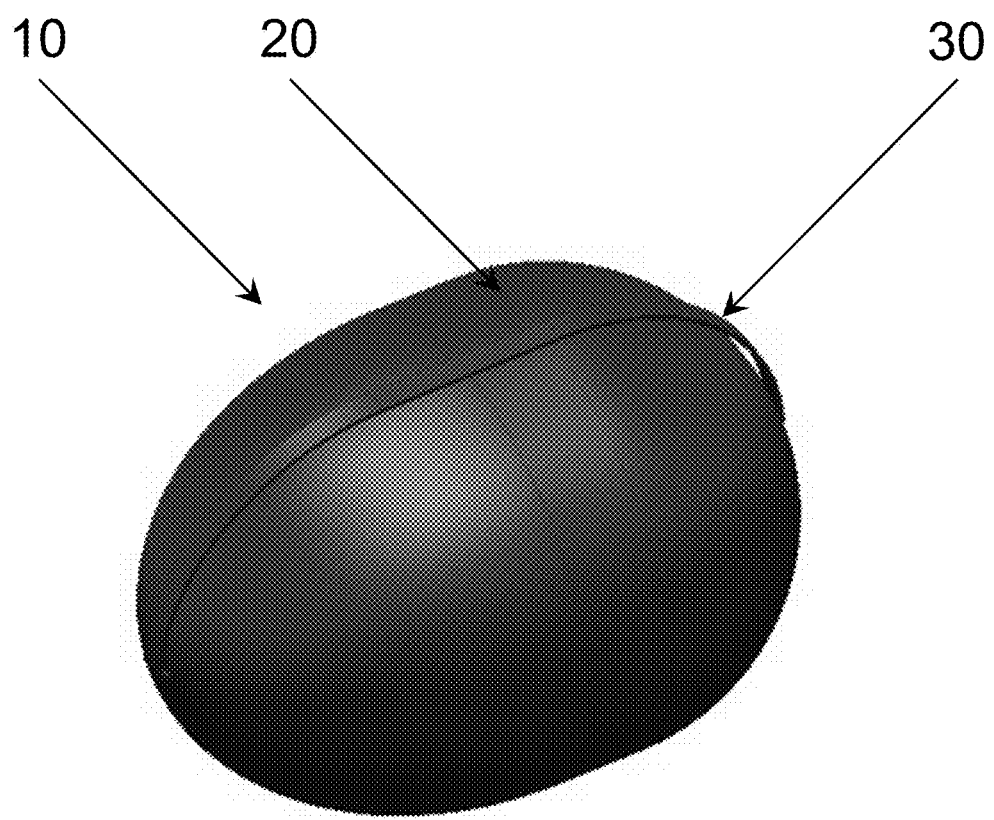
FIG. 1 is a perspective view of an embodiment of a device for alleviating dyspareunia constructed in accordance with principles of the present disclosure, viewed from a first side thereof.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF EXEMPLARY EMBODIMENTS

The present disclosure is directed to embodiments of a device for alleviating dyspareunia. Embodiments of a device for alleviating dyspareunia can comprise a pliable body filled with a resilient and soft material, such as, medical grade silicone, for example. In embodiments, the body can be a rounded shape, including ovoid or annular. The body can be configured to act as a buffer or shock absorber for the upper vagina and cervix. The resilient nature of the pliable body allows forces to be displaced laterally instead of cephalad, to thereby help alleviate pain by relieving pressure on the cervix, cardinal and uterosacral ligaments, vaginal apex, etc.

In embodiments of a device for alleviating dyspareunia constructed according to principles of the present disclosure, the device can include a retrieval strap attached to the pliable body in order to facilitate the removal of the device. In use, the retrieval strap can be positioned so that it can be grasped by one or more fingers to permit the device to be pulled from the vagina without having to grasp the body itself.

Embodiments of a device for alleviating dyspareunia constructed according to principles of the present disclosure can be used by being placed by the user or her partner within the vagina prior to intercourse. After placement in the vagina, the device can be advanced cephalad with fingers or the penis until gentle resistance is met. Once intercourse is complete, the device can be removed, such as by grasping the attached strap and gently pulling it from the vagina. After use, the device can be cleaned, such as by being washed with soap and water, and allowed to dry. The device can be stored in a dry, room temperature environment until the next use.

In embodiments of a kit constructed in accordance with principles of the present disclosure, the kit includes a plurality of devices for alleviating dyspareunia constructed in accordance with principles of the present disclosure wherein each one of the devices is a different size. In embodiments, the kit includes three differently-sized devices (e.g., devices with bodies that weigh approximately 55 gm, 85 gm, and 120 gm, respectively). In use, a user can select one of the differently-sized devices according to user preference or a prescribed protocol. For example, in use, a user may use the smallest-sized device initially in order to get comfortable with the insertion and removal of the device and then over the course of a series of subsequent uses progress to the larger sizes as desired. In embodiments, the user can ultimately decide which of the differently-sized devices is preferred (e.g., because the size fits best for her and/or produces the greatest alleviation of pain during intercourse). In embodiments, a single device for alleviating dyspareunia constructed in accordance with principles of the present disclosure can be packaged for individual sale.

Figure 2:
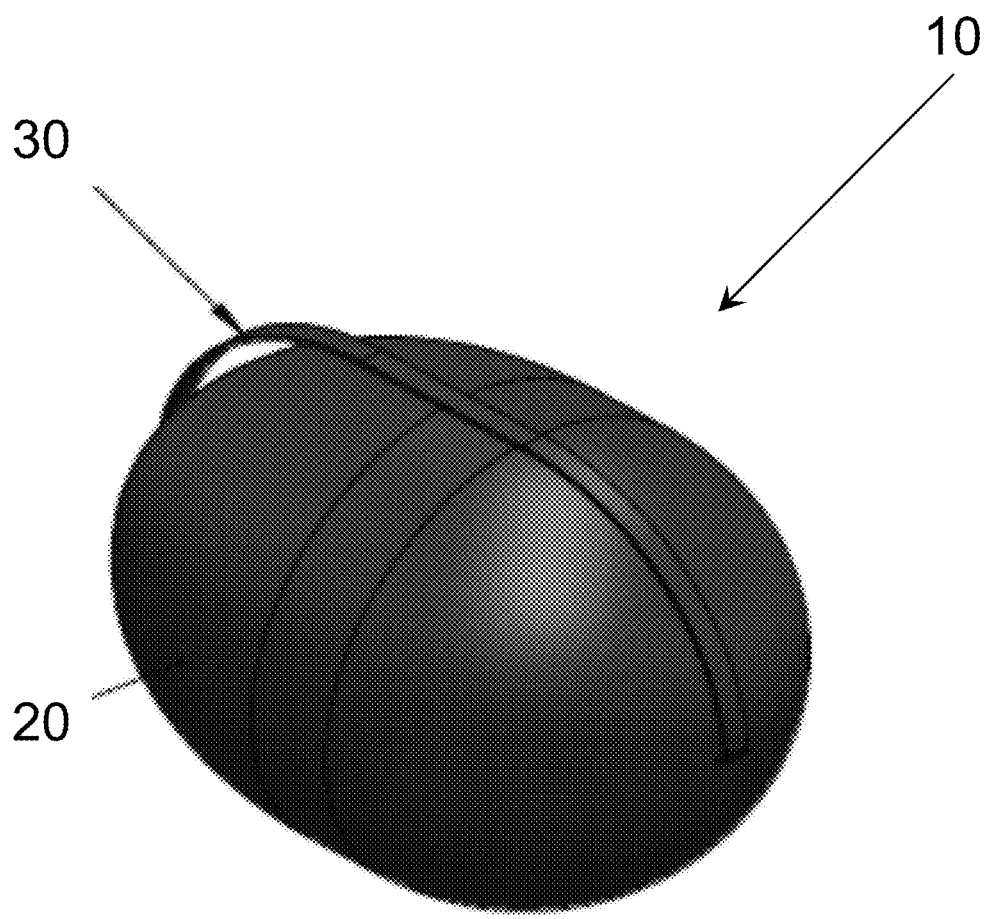
FIG. 2 is another perspective view of the device of FIG. 1, viewed from a second side thereof.
Figure 3:
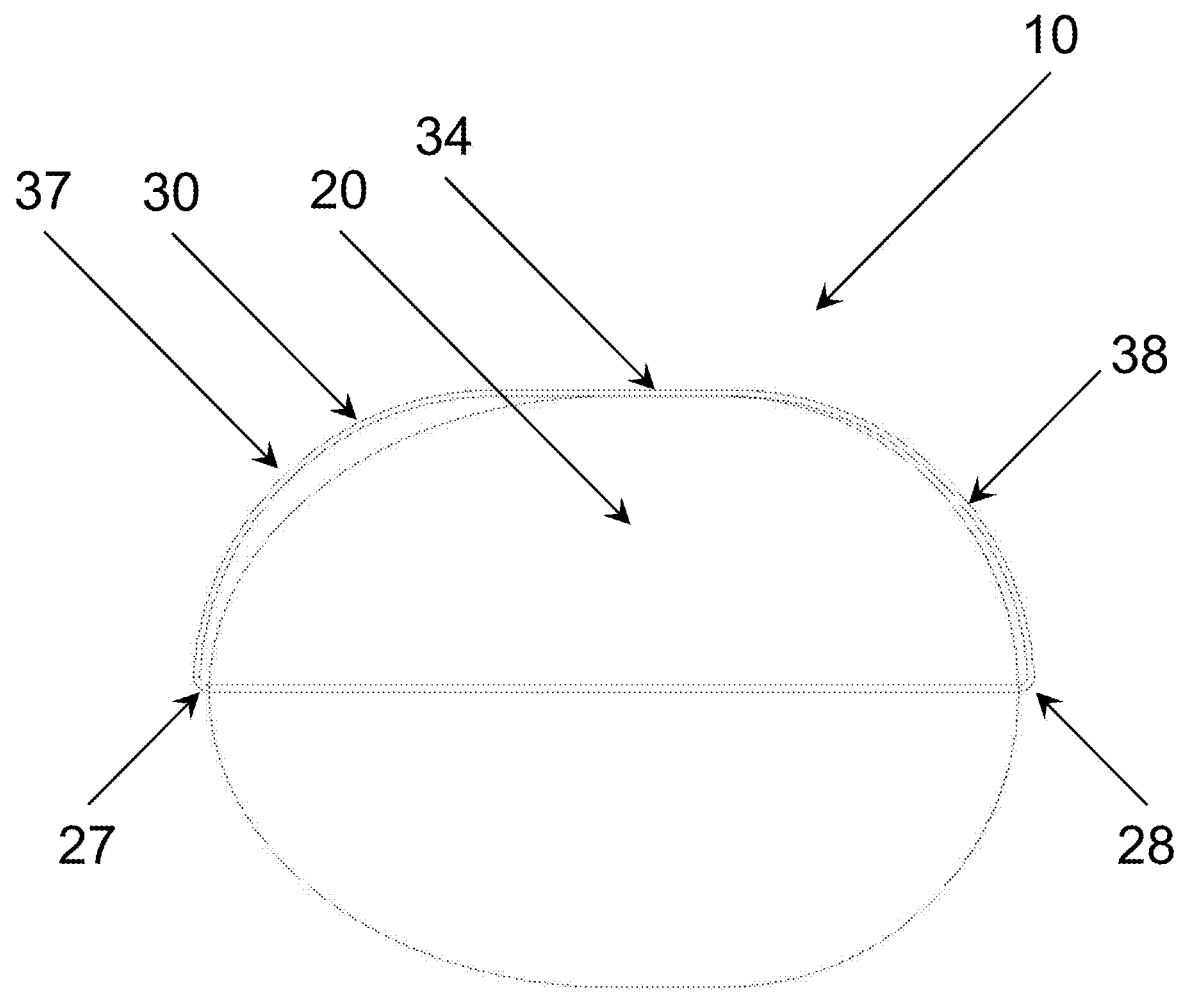
FIG. 3 is an elevational view of the device of FIG. 1, viewed from the second side thereof.

Turning now to the Figures, an embodiment of a device for alleviating dyspareunia 10 constructed according to principles of the present disclosure is shown in FIGS. 1-3. In the illustrated embodiment, the device 10 includes a body 20 and a retrieval strap 30 mounted to the body 20.

Figure 4:
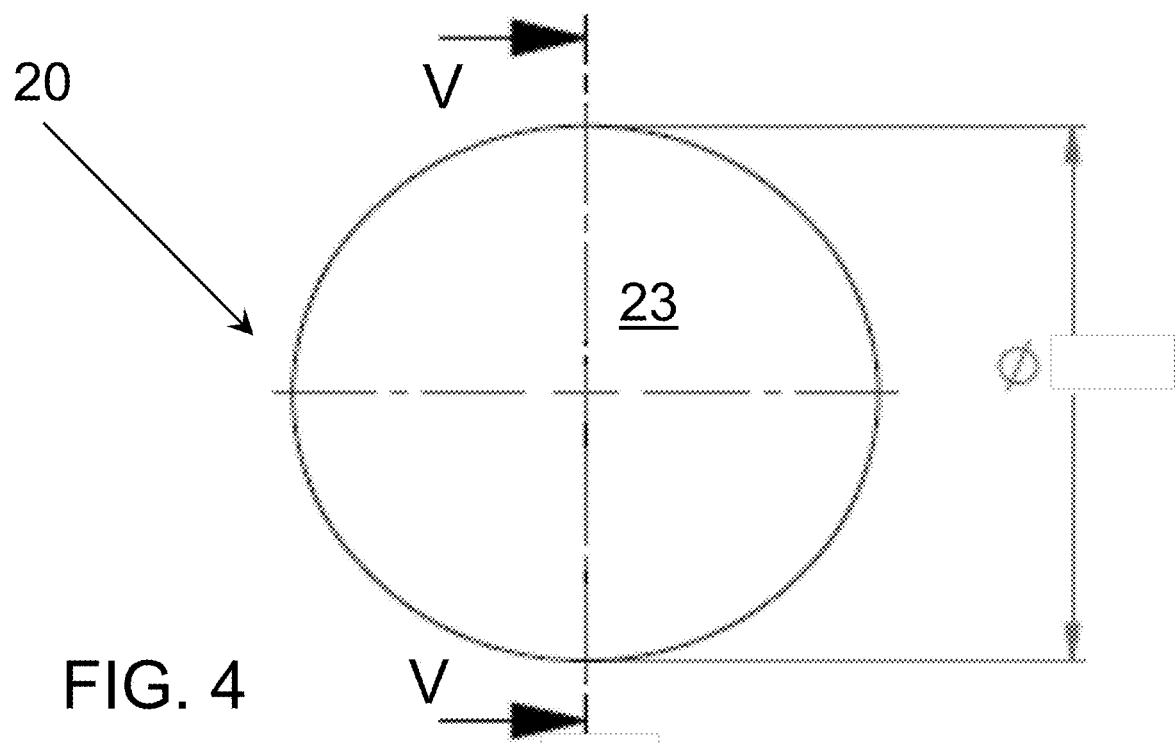
FIG. 4 is an end elevational view of a body of the device of FIG. 1.
Figure 5:
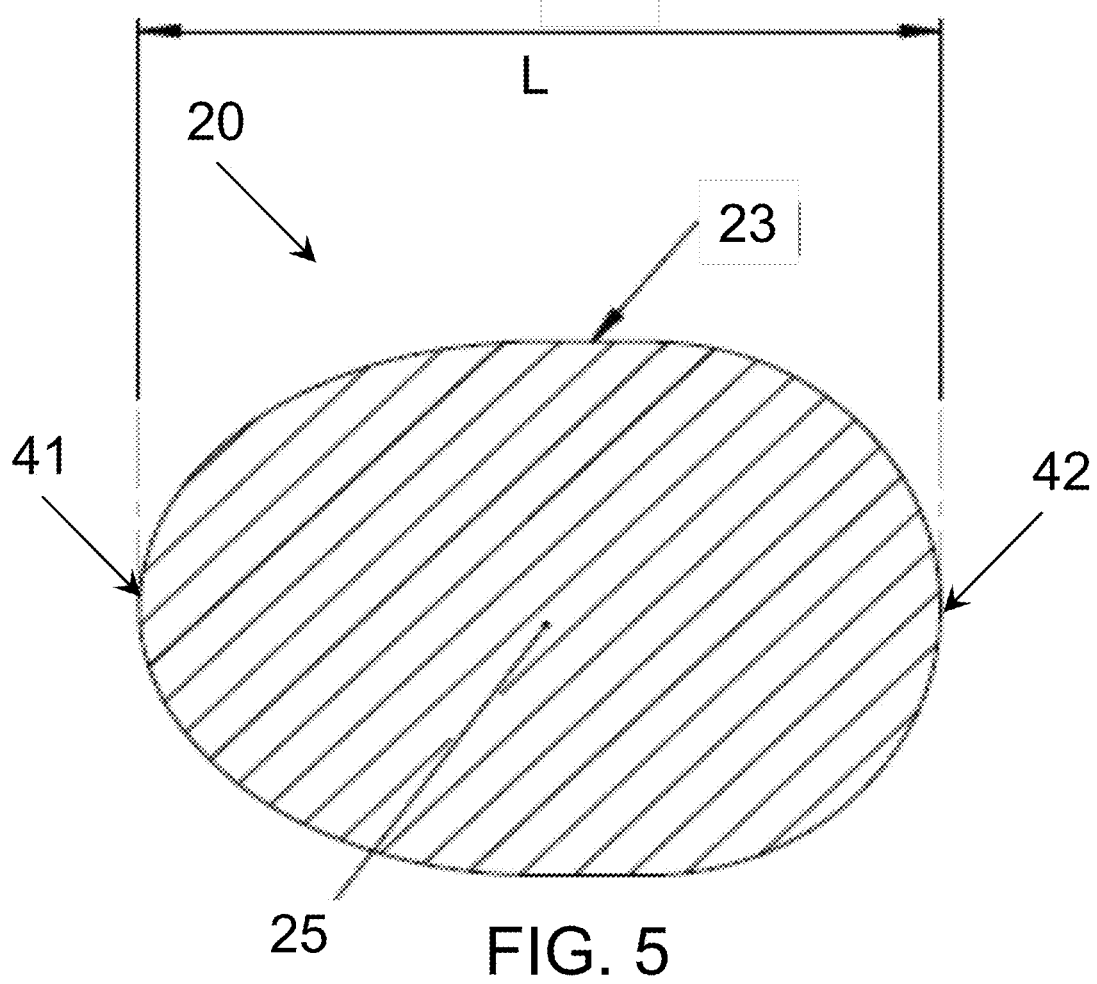
FIG. 5 is a cross-sectional view of the body taken along line V-V in FIG. 4.

Referring to FIGS. 3-5, the body 20 can be made from any suitable material such that the body 20 is configured to absorb energy when impacted. In embodiments, the body 20 is configured to absorb impact energy when situated within a user's vagina such that cervical and/or upper vaginal pain (dyspareunia) is alleviated during intercourse. The illustrated body 20 is ovoid or egg-shaped. In other embodiments, the body 20 can have a different size and/or shape.

Referring to FIGS. 4 and 5, the body 20 extends from a first end 41 to a second end 42 over a length L. The body 20 has a maximum diameter Ø in a plane transverse to its length L. In embodiments, a ratio of the length L to the maximum diameter Ø is in a range between 1 and 1.5. In other embodiments, a ratio of the length L to the maximum diameter Ø is in a range between 1.2 and 1.5. In still other embodiments, a ratio of the length L to the maximum diameter Ø is in a range between 1.2 and 1.4. In yet other embodiments, a ratio of the length L to the maximum diameter Ø is in a range between 1.25 and 1.4.

The illustrated body 20 includes an outer skin 23 and an inner core 25 disposed within the skin 23. The skin 23 comprises an outer exterior surface of the body 20 that defines the shape of the body 20. The core 25 is disposed within the skin 23.

In embodiments, the skin 23 can be made from any suitable material, such as a suitable elastomeric material. In embodiments, the skin 23 can be made from an elastomeric material that has a hardness in a range from 10 to 40 Shore A as measured by ASTM D2240, from 20 to 40 Shore A in other embodiments, from 25 to 40 Shore A in still other embodiments, and from 30 to 40 Shore A in yet other embodiments. In embodiments, the skin 23 can be made from a suitable silicone material, such as a suitable medical-grade room-temperature-vulcanizing (RTV) silicone, for example. In embodiments, the skin 23 can be made by any suitable process, such as by, spin cast molding or other suitable molding technique, for example.

In embodiments, the core 25 can be made from any suitable material, such as a suitable elastomeric material. In embodiments, the core 25 can be made from a material that is different from that which the skin 23 is made. In embodiments, the core 25 can be made from a material (or materials) such that the core 25 is softer than skin 23. In embodiments, the core 25 can be made from an elastomeric material that has a hardness in a range from 10 Shore 00 to 40 Shore A as measured by ASTM D2240, and from 10 Shore 00 to 10 Shore A in still other embodiments.

In embodiments, the skin 23 and the core 25 are both made from a composition that comprises a silicone. The silicone used in the core 24 is different from the silicone used in the skin 23 with respect to at least one property parameter, such as, hardness, for example.

In embodiments, the core 25 can be made from a suitable silicone material, such as a suitable medical-grade silicone gel, for example. In embodiments, the pliability and resilience of the core 25 can be controlled by making the core from a composition including an elastomeric gel and a "deadening" material that has physical properties adapted to reduce the resilient rebound or bounce back of the core 25, as will be understood by one skilled in the art. In embodiments, the core 25 can be made from a composition including an elastomeric material and a suitable deadening material, such as those commercially-available for use in a prosthetic, such as, a commercially-available flesh 10 deadener, for example. In embodiments, the flesh 10 deadener is present in the composition of the core 25 in varying concentrations to provide the desired energy absorption during impact for a desired rebound or bounce back time. In embodiments, the deadening material has a pph (parts per hundred) in a range from 10 to 40, and in a range from 20 to 40 in other embodiments.

In embodiments, the core 25 can be configured such that it has a resilience performance characteristic that promotes a relatively slow rebound as discussed in greater detail below. In embodiments, skin 23 and the core 25 can be constructed such that the body 20 has a modulus of elasticity in a range between 5 kPa and 10 kPa.

In embodiments, the core 25 can be made by any suitable process, such as by, preparing the material to be used for the core 25 and injecting the core material into the interior of the skin 23, such as by being dispensed through a suitable syringe needle inserted into the interior of the skin 25, for example. Suitable processing techniques can be employed while the skin 23 and core 25 cure in order to produce the desired shape of the body 20.

Figure 6:
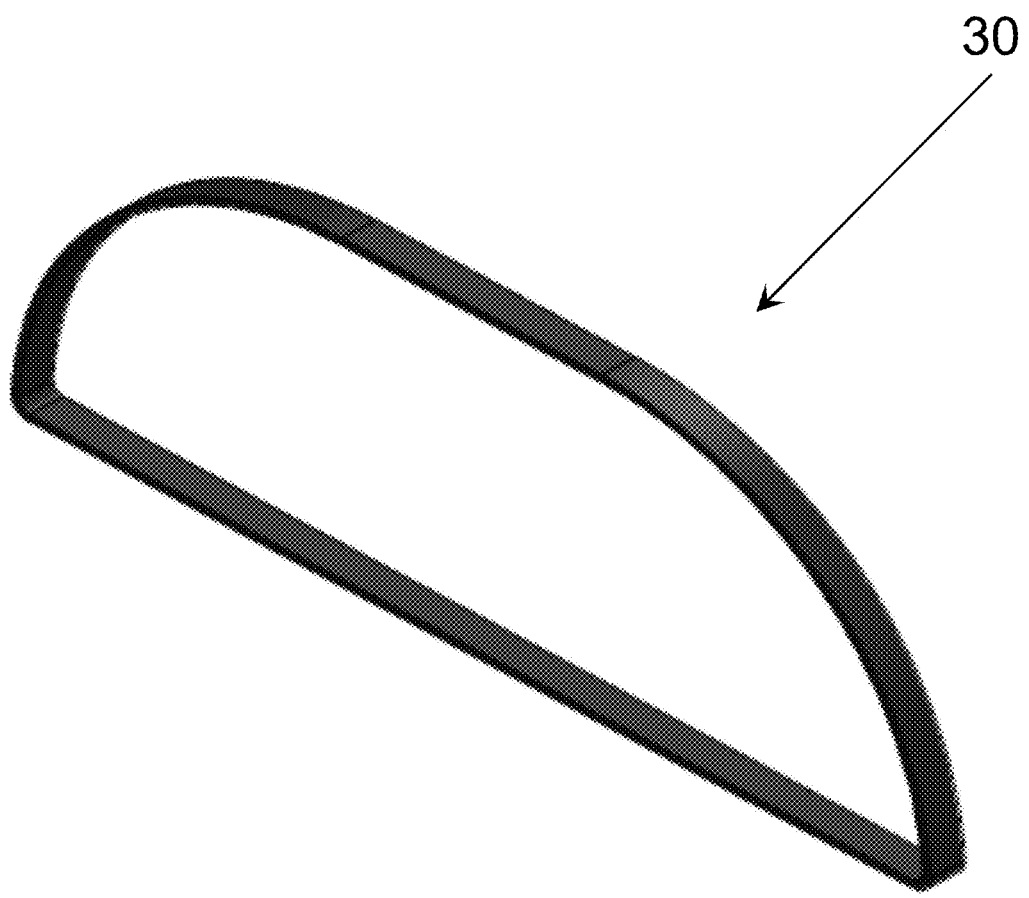
FIG. 6 is a perspective view of a retrieval strap of the device of FIG. 1.

Referring to FIG. 6, the strap 30 can be provided to aid in the removal of the device 10 from a user's vagina. The illustrated strap 30 is in the form of a continuous loop that can extend through the body 20. In other embodiments, the strap 30 can have a different configuration. Referring to FIG. 6, the illustrated strap 30 is in the form of a braided tape with a width of about 3.5 mm and is made from ultra-high molecular weight polyethylene (UHMWPE).

In embodiments, the strap 30 can be made from any suitable material, such as a suitable elastomeric material. In embodiments, the strap 30 can be made from a braided thermoplastic material suitable for use as a suture.

In embodiments, the strap 30 can be made from an elastomeric material that has a hardness in a range from 10 to 40 Shore A as measured by ASTM D2240. In embodiments, the strap 30 can be made from an elastomeric material that has a hardness that is harder than the material from which the body 20 is made. In embodiments, the strap 30 is made from an elastomeric material that has a hardness greater than the hardness of the composition used for the skin 23 and the composition used for the core 25. In embodiments, the strap 30 can be made from a suitable silicone material, such as a suitable medical-grade silicone, for example.

In embodiments, the strap 30 can be made from a suitable thermoplastic material, such as polyethylene. In embodiments, the strap 30 can be made from a braided thermoplastic material suitable for use as a suture. In embodiments, the strap 30 can be made as a braided tape from ultra-high molecular weight polyethylene (UHMWPE), such as a suitable commercially-available braided suture tape. In embodiments, the strap 30 can be made as a braided tape from UHMWPE and have a width in a range from 1 mm to 5 mm. In embodiments, the strap 30 can be made by any suitable process, such as by, molding, for example.

Referring to FIG. 3, in embodiments, to mount the strap 30 to the body 20, a pair of end incisions can be made through the skin 23 to define insertion points 27, 28 on opposing ends of the body 20. Before being fabricated into a continuous loop, the strap 30 can includes a pair of discontinuous ends, and one of which can be inserted into one insertion point 27 and out through the other 28. The ends of the strap 30 can be connected together via any suitable technique, such as by using a suitable adhesive, for example. The bonded connection joint between the ends of the strap 30 can be positioned within the body 20.

Referring to FIG. 3, an intermediate portion 34 of the strap 30 can be adhered to the skin 23 of the body 20 to retain the strap 30 in place. First and second finger loop portions 37, 38 are defined between the intermediate portion 34 and the insertion points 27, 28 of the body 20 such that a user can insert either end of the device 10 (as defined by the insertion points 27, 28) into the user's vagina and be able to use the loop portion at the other end of the device 10 to facilitate removal.

Figure 7:
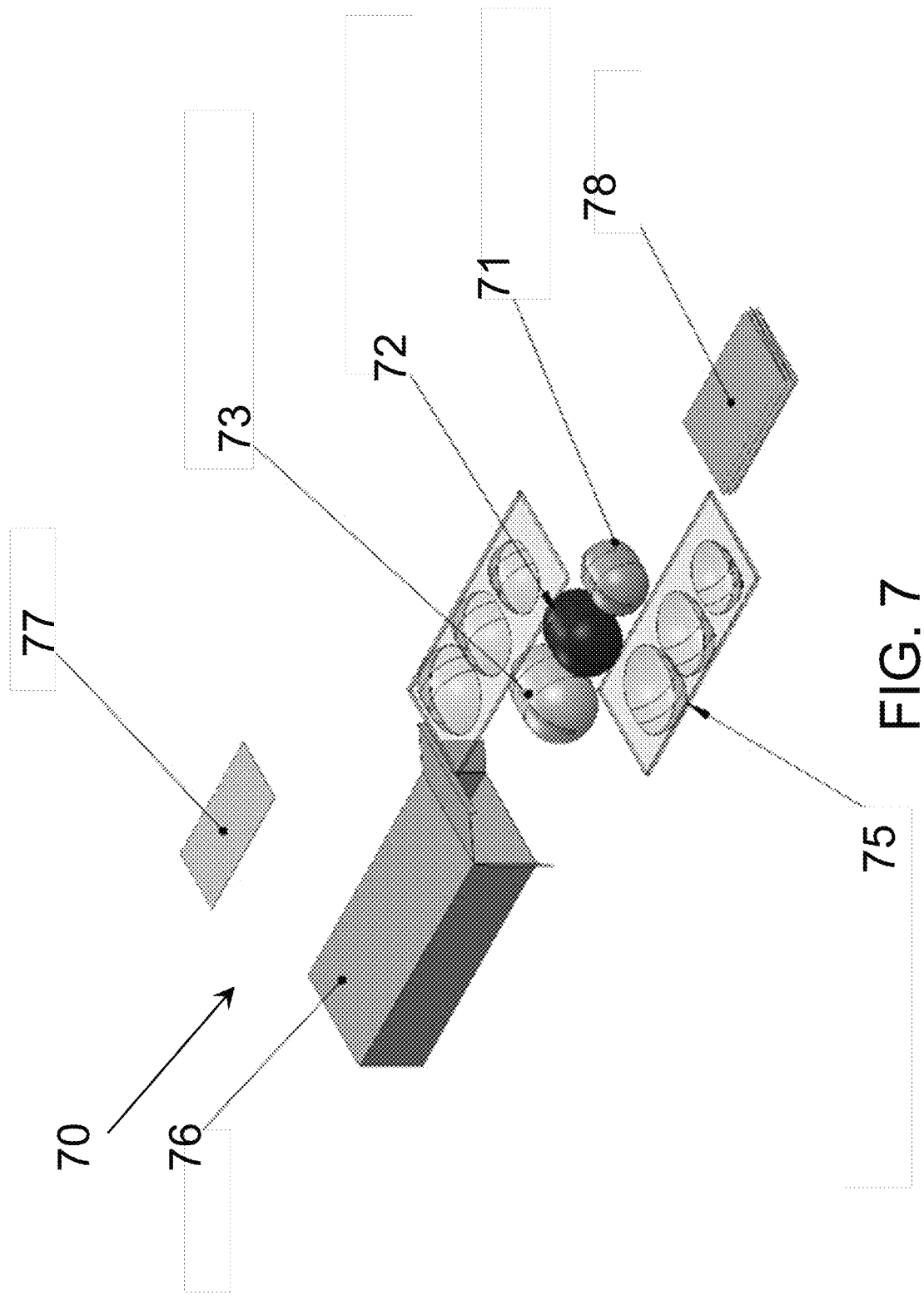
FIG. 7 is an exploded view of an embodiment of a kit constructed in accordance with principles of the present disclosure, the kit including a plurality of devices for alleviating dyspareunia constructed in accordance with principles of the present disclosure each one being a different size.

Referring to FIG. 7, there is shown an embodiment of a kit 70 constructed in accordance with principles of the present disclosure. In embodiments, the kit 70 includes a plurality of devices 71, 72, 73 for alleviating dyspareunia constructed in accordance with principles of the present disclosure wherein each one is a different size. In the illustrated embodiment, the kit 70 includes three devices 71, 72, 73 that are similar in construction to the device 10 shown in FIGS. 1-6 but are differently-sized devices with bodies that weigh approximately 55 gm, 85 gm, and 120 gm, respectively. In other embodiments, the kit 70 includes another number of differently-sized devices (e.g., two or four differently-sized devices).

In the illustrated embodiment, the kit 70 includes a tray assembly 75 to house the devices and a carton 76 within which the tray assembly 75 can be inserted. Suitable labels 77 and information booklets 78 can also be supplied with the devices 71, 72, 73 that are configured to provide information concerning the use and care of the devices 71, 72, 73.

In use, a user can select one of the differently-sized devices 71, 72, 73 according to user preference or a prescribed protocol. For example, in use, a user may use the smallest-sized device 71 initially in order to get comfortable with the insertion and removal of the device 71 and then over the course of a series of subsequent uses progress to the larger sizes 72, 73 as desired. In embodiments, the user can ultimately decide which of the differently-sized devices 71, 72, 73 is preferred (e.g., because the size fits best for her and/or produces the greatest alleviation of pain during intercourse).

In embodiments, a kit constructed in accordance with principles of the present disclosure can include a plurality of devices for alleviating dyspareunia constructed in accordance with principles of the present disclosure that are all the same size. In embodiments, a single device for alleviating dyspareunia constructed in accordance with principles of the present disclosure can be packaged for individual sale.

Figure 8:
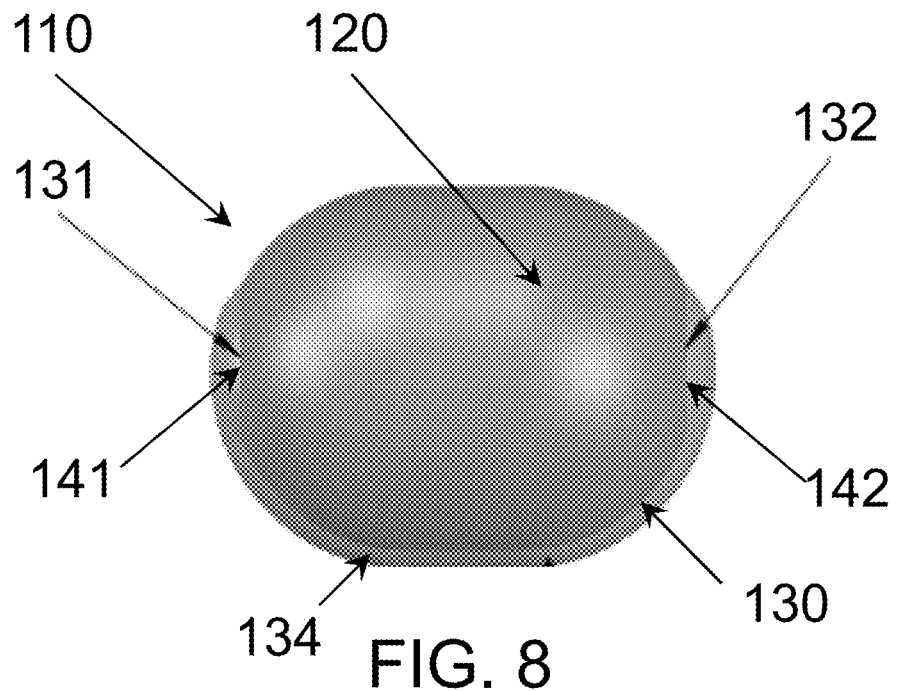
FIG. 8 is a plan view of another embodiment of a device for alleviating dyspareunia constructed in accordance with principles of the present disclosure.
Figure 9:
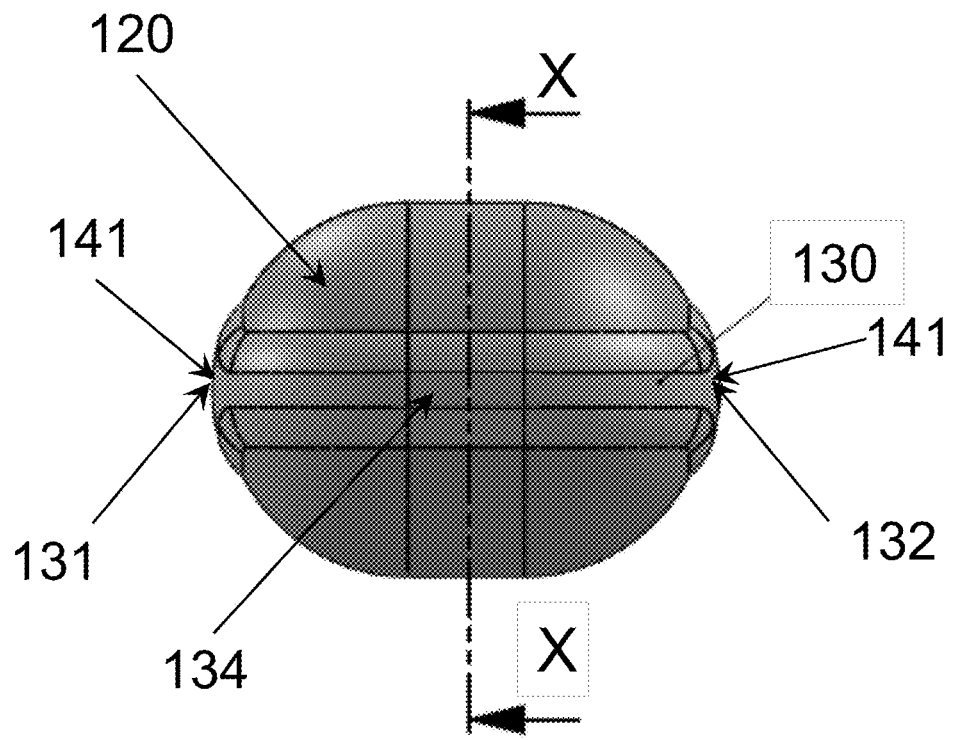
FIG. 9 is an end elevational view of the device of FIG. 8.
Figure 10:
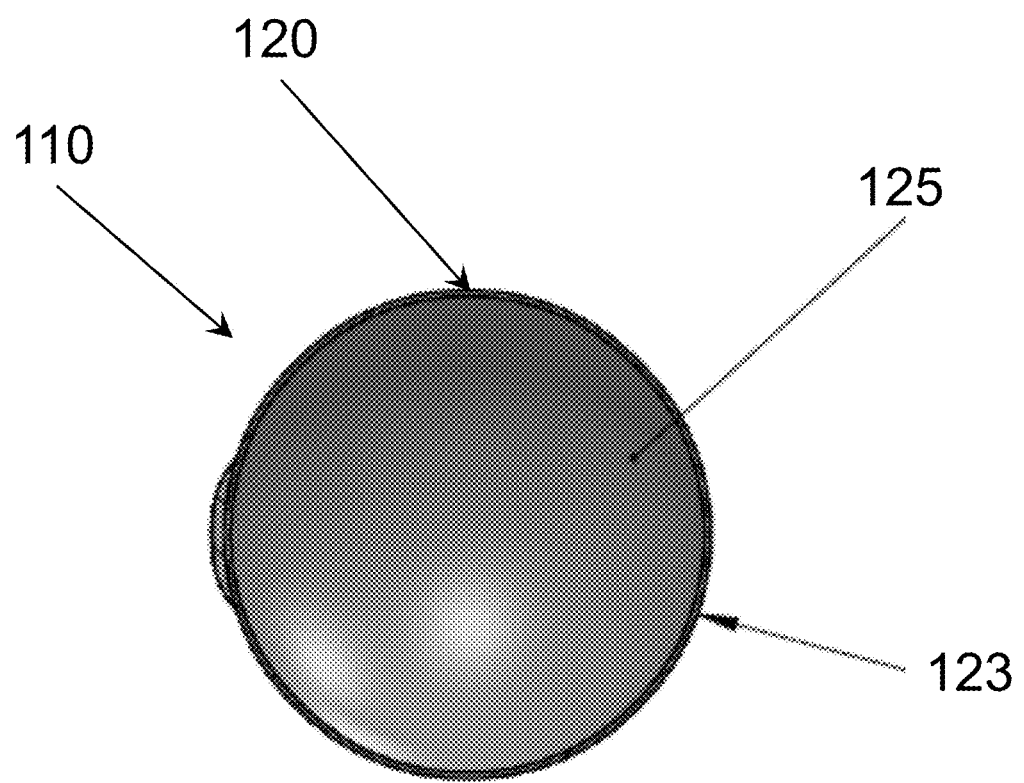
FIG. 10 is a cross-sectional view of the device of FIG. 8 taken along line X-X in FIG. 9.

Referring to FIGS. 8-10, there is shown another embodiment of a device 110 for alleviating dyspareunia constructed in accordance with principles of the present disclosure. In the embodiment illustrated in FIGS. 8-10, the device 110 includes a body 120 and a retrieval strap 130 mounted to the body 120. The illustrated body 120 is ovoid or egg-shaped and includes a skin 123 that defines the shape of the body 120 and a core 125 disposed within the skin 123. The strap 130 can be provided to aid in the removal of the device 110 from a user's vagina. The illustrated strap 130 is in the form of a strip or band.

Referring to FIGS. 8 and 9, in embodiments, the body 120 can include opposing ends 141, 142 that are substantially similar to each other to provide a symmetrical body 120 about a central plane as indicated by Section X-X in FIG. 9. In embodiments, the opposing ends 141, 142 can have different shapes from each other. For example, the ends 141, 142 can have different shapes such that the body 120 is substantially egg-shaped, such as shown in FIG. 5.

Figure 11:
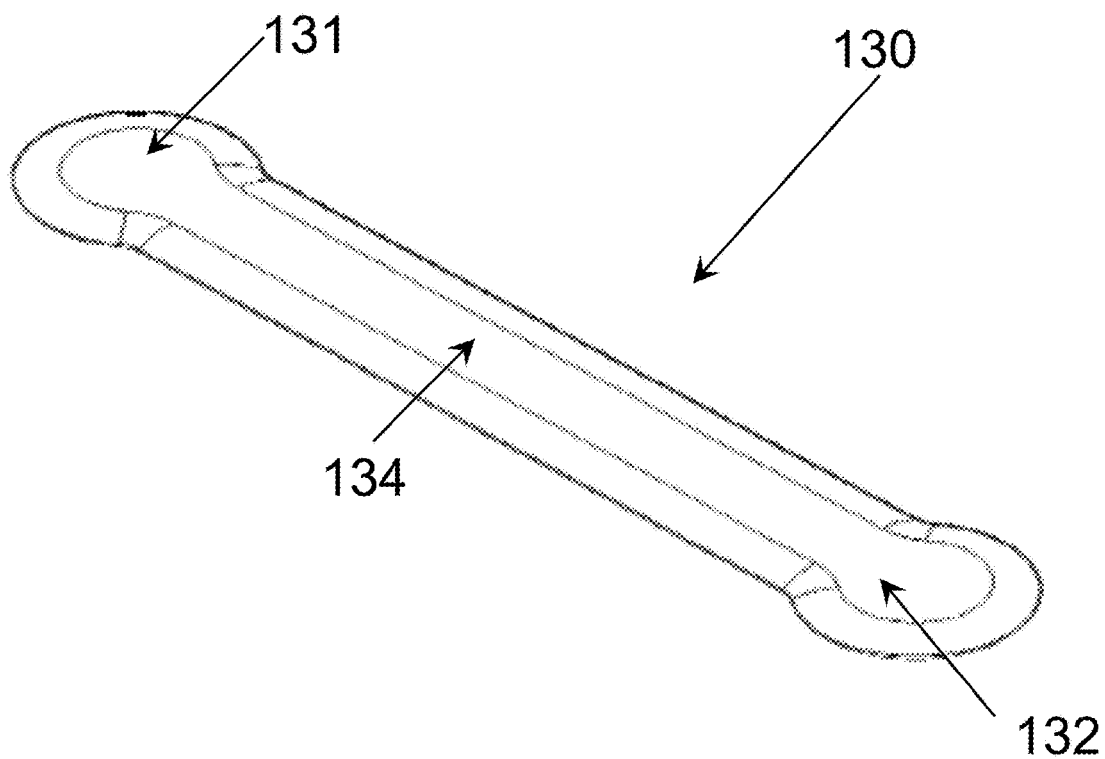
FIG. 11 is a perspective view of a strap of the device of FIG. 8.
Figure 12:
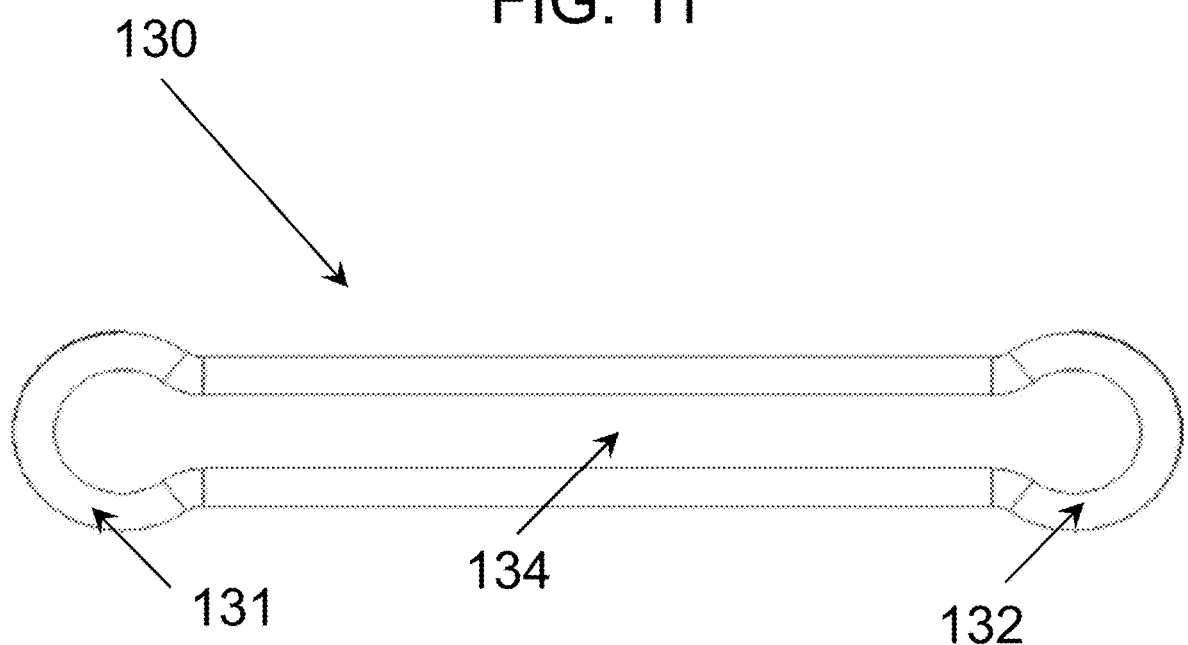
FIG. 12 is a plan view of the strap of FIG. 11.

Referring to FIGS. 11 and 12, the strap 130 of the device 110 of FIGS. 8-10 includes first and second ends 131, 132 that are in opposing relationship to each other with an intermediate portion 134 disposed therebetween. The first and second ends 131, 132 of the strap 130 are generally round and are configured to be secured to selected portions of the skin 123 of the body 120. The strap 130 can be made from a suitable elastomeric material. The strap 130 is elongated.

Referring to FIGS. 8 and 9, in the illustrated embodiment, the first and second ends 131, 132 of the strap 130 are mounted to the opposing ends 141, 142 of the body 120. In embodiments, the first end 131 and the second end 132 are configured to be connected to the body 120 at a first point and a second point, respectively, where the first point is discontinuous from the second point, such as is shown in FIG. 9. The intermediate portion 134 of the strap 30 is not connected to the body 120 such that the intermediate portion 134 provides a finger loop that can be grasped in order to facilitate the removal of the device 11 from a user's vagina.

The construction and/or use of the device 110 of FIGS. 8-12 can be similar in other respects to the device 10 of FIGS. 1-6.

Referring to FIGS. 13-16, there is shown another embodiment of a device 210 for alleviating dyspareunia constructed in accordance with principles of the present disclosure. In the embodiment illustrated in FIGS. 13-16, the device 210 includes a body 220 and a retrieval strap 230 mounted to the body 220 via first and second mounting buttons 251, 252. The illustrated body 220 is annular or ring-shaped. The strap 230 can be provided to aid in the removal of the device 210 from a user's vagina.

Figure 13:
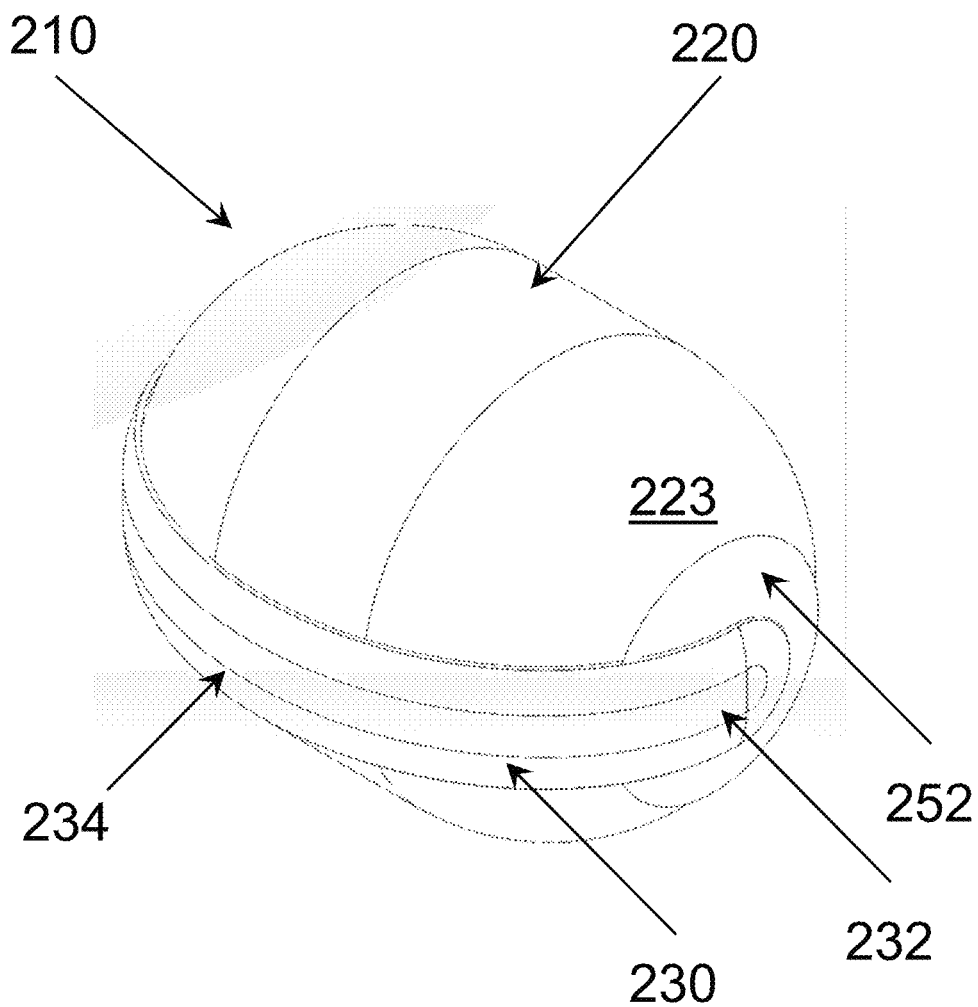
FIG. 13 is a plan view of still another embodiment of a device for alleviating dyspareunia constructed in accordance with principles of the present disclosure.
Figure 14:
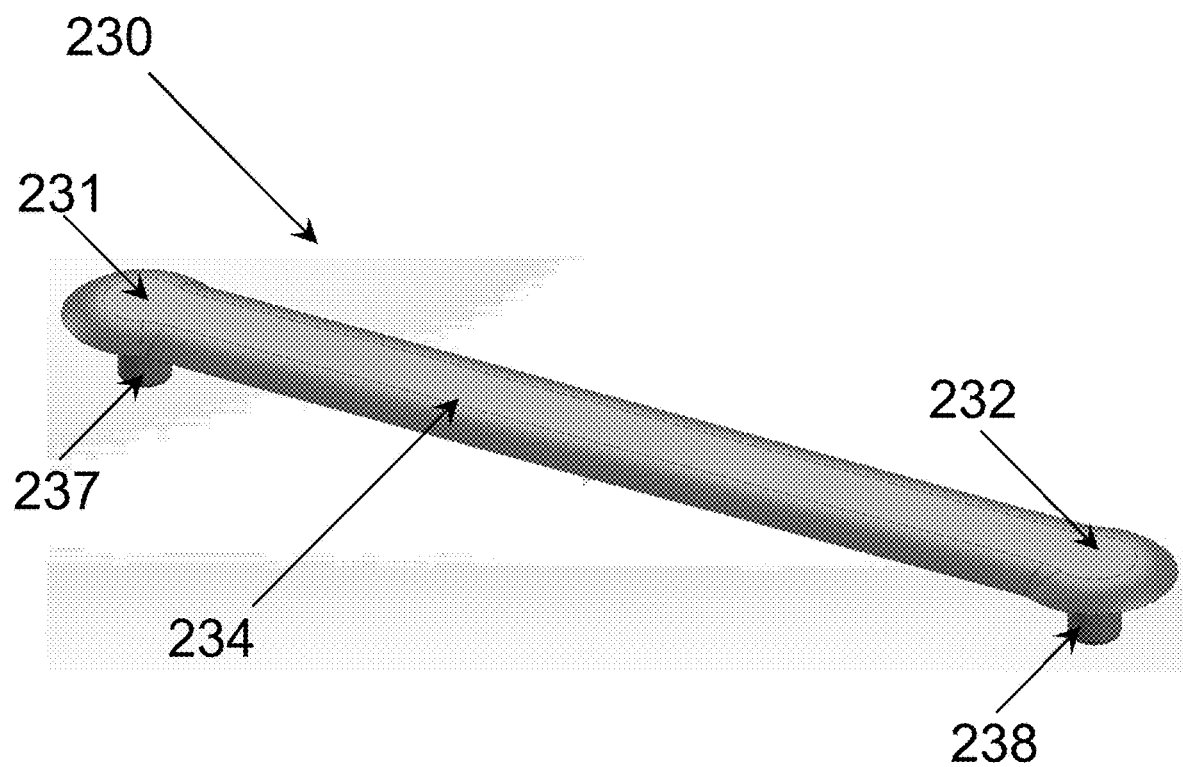
FIG. 14 is a perspective view of a strap of the device of FIG. 13.

Referring to FIG. 14, the illustrated strap 230 of the device 210 of FIG. 13 includes first and second ends 231, 232 that are in opposing relationship to each other with an intermediate portion 234 disposed therebetween. The first and second ends 231, 132 of the strap 230 are generally round and are configured to be secured to selected portions of the skin 223 of the body 220. The strap 230 can be made from a suitable elastomeric material. The strap 230 is elongated and in the form of a strip or band. The strap 230 is connected at its distal ends 231, 232 to the body 220 such that the intermediate portion 234 is not connected to the body 220. Referring to FIG. 13, the intermediate portion 234 can be flexed away from the body 220 to define a finger loop therebetween able to accommodate at least one finger therethrough to facilitate the removal of the device 210 from a user's vagina.

Figure 15:
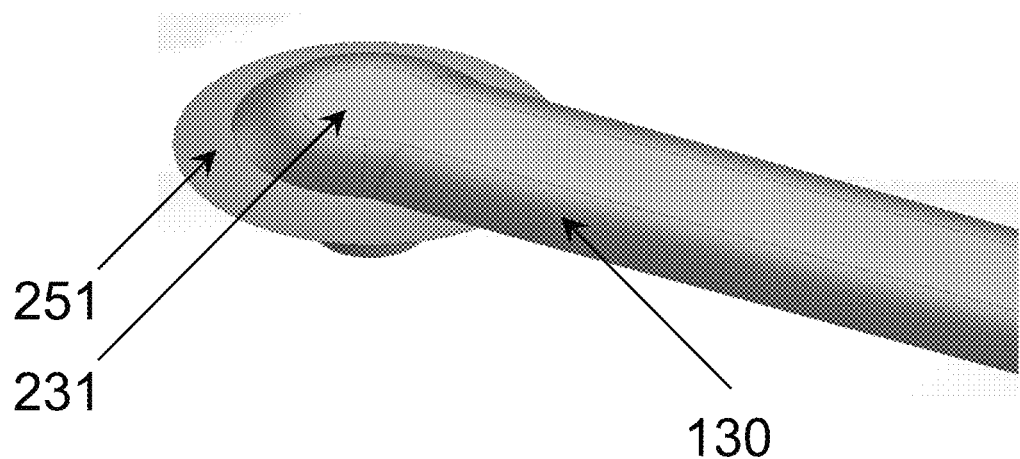
FIG. 15 is a fragmentary, perspective view of a first end of the strap of FIG. 14 and a first mounting button of the device of FIG. 13 mounted to a post projecting from the first end of the strap.
Figure 16:
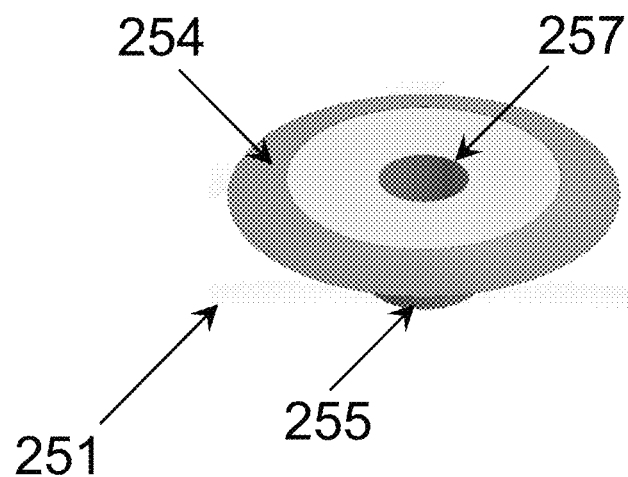
FIG. 16 is a perspective view of the first mounting button of the device of FIG. 8.

Referring to FIGS. 14-16, he first and second ends 231, 232 of the strap 230 each includes a post 237, 238 projecting therefrom. The posts 237, 238 are configured to respectively engage with the first and second mounting buttons 251, 252 to facilitate the mounting of the strap 230 to the body 220. The posts 237, 238 and mounting buttons 251, 252 are configured to help with the alignment of the strap 230 upon the body 220 and the bonding of the strap 230 to the body 220.

Referring to FIGS. 15 and 16, the first mounting button 251 is shown. The first and second mounting buttons 251, 252 are constructed in a similar manner. Accordingly, it should be understood that the description of the first mounting button 251 is applicable to the second mounting button 252, as well. The first mounting button 251 includes a disc 254 and a cylindrical stem 255 projecting from the disc 254. The mounting button 251 defining a central opening 257 through the disc 254 and the stem 255. The central opening 257 and the cylindrical stem 255 are configured to receive one of the posts 237, 238 of the strap 230 therein.

The first and second mounting buttons 251, 252 are respectively mounted to the body 220 at first and second points thereof using any suitable technique (such as a suitable adhesive, e.g.) such that the cylindrical stems 255 extend through openings in the skin 223 of the body 220. The first mounting button 251 can be interposed between the body 220 and the first end 231 of the strap 230 such that the post 237 projecting from the first end 231 of the strap 230 extends through the central opening 257 of the first mounting button 251. And the second mounting button 252 can be interposed between the body 220 and the second end 232 of the strap 230 such that the post 238 projecting from the second end 232 of the strap 230 extends through the central opening 257 of the second mounting button 252. In embodiments, first and second ends 231, 232 of the strap 230 can be secured to the first and second mounting buttons 251, 252, respectively, using any suitable technique (such as a suitable adhesive, e.g.).

The construction and/or use of the device 210 of FIGS. 13-16 can be similar in other respects to the device 10 of FIGS. 1-6 and/or the device 110 of FIGS. 8-12.

Figures 17, 18:
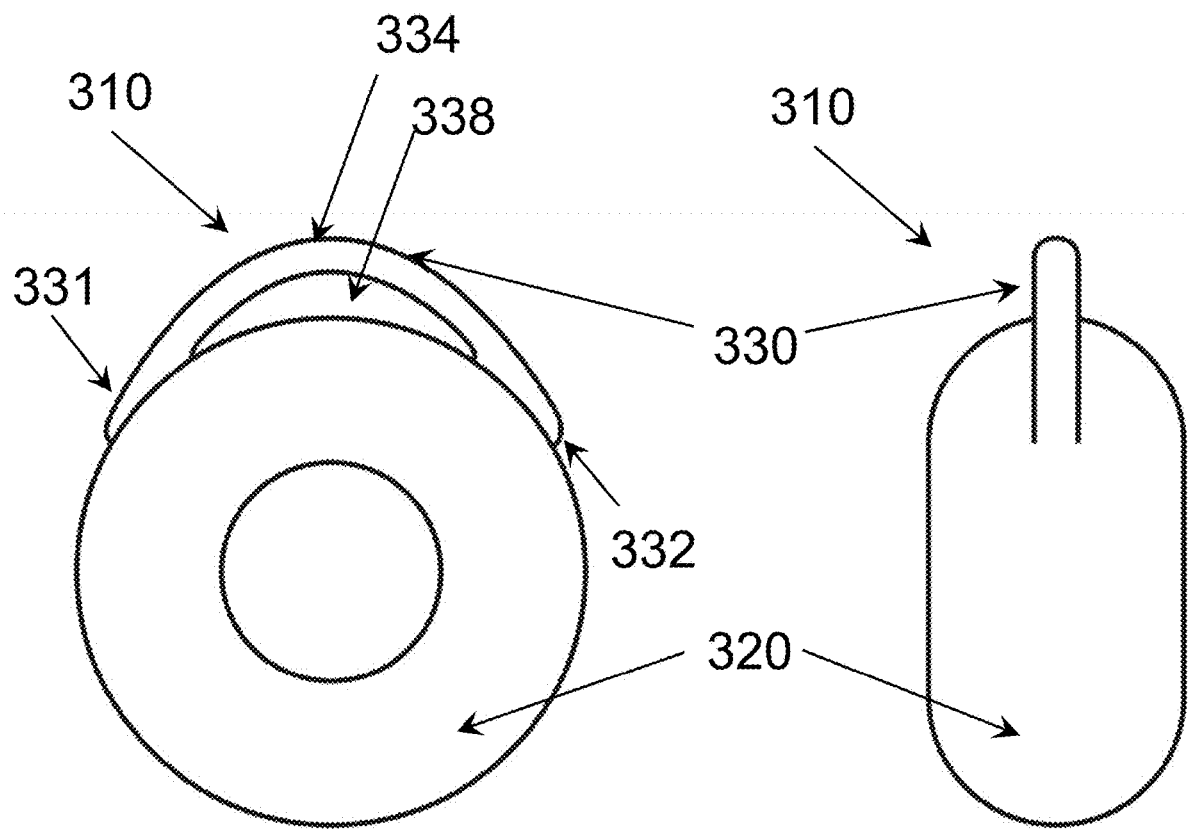
FIG. 17 is a plan view of still another embodiment of a device for alleviating dyspareunia constructed in accordance with principles of the present disclosure.
FIG. 18 is a side elevational view of the device of FIG. 17.
Figure 19:
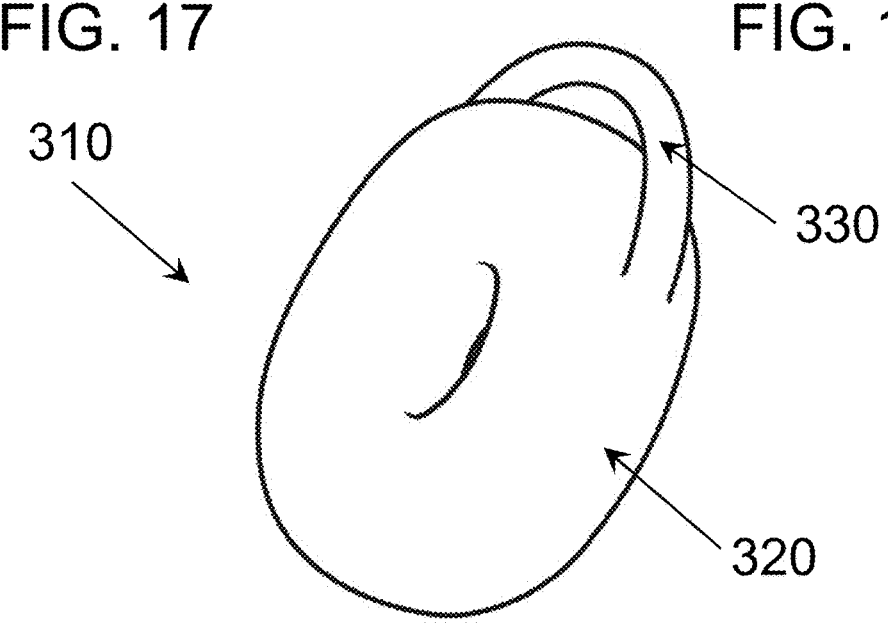
FIG. 19 is a perspective view of the device of FIG. 17.

Referring to FIGS. 17-19, there is shown another embodiment of a device 310 for alleviating dyspareunia constructed in accordance with principles of the present disclosure. In the embodiment illustrated in FIGS. 17-19, the device 310 includes a body 320 and a retrieval strap 330 mounted to the body 320. The illustrated body 320 is annular or ring-shaped. The strap 330 can be provided to aid in the removal of the device 310 from a user's vagina. The illustrated strap 330 is in the form of a strip or band with a pair of distal ends 331, 332 and an intermediate portion 334 therebetween. The strap 330 is connected at its distal ends 331, 332 to the body 320 such that the intermediate portion 334 is not connected to the body 320 so that the intermediate portion 334 defines a finger loop 338 (see FIG. 17). The construction and/or use of the device 310 of FIGS. 17-19 can be similar in other respects to the device 10 of FIGS. 1-6, the device 110 of FIGS. 8-12, and/or the device of FIGS. 13-16.

Figure 20:
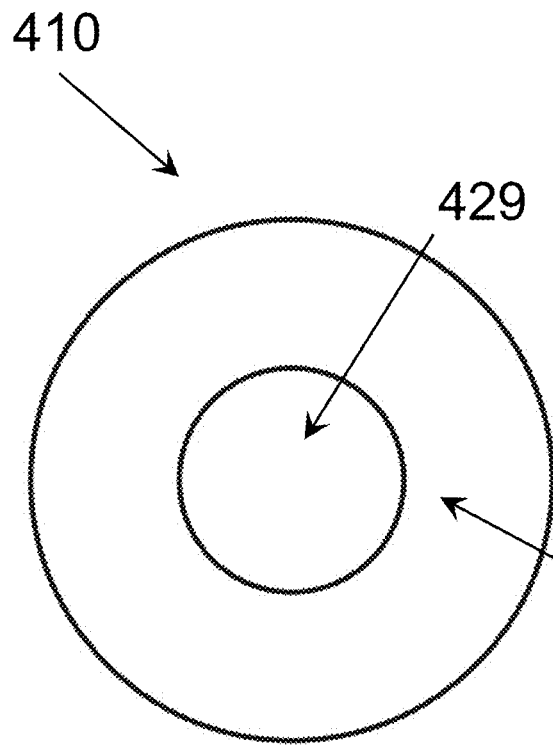
FIG. 20 is a plan view of still another embodiment of a device for alleviating dyspareunia constructed in accordance with principles of the present disclosure.
Figure 21:
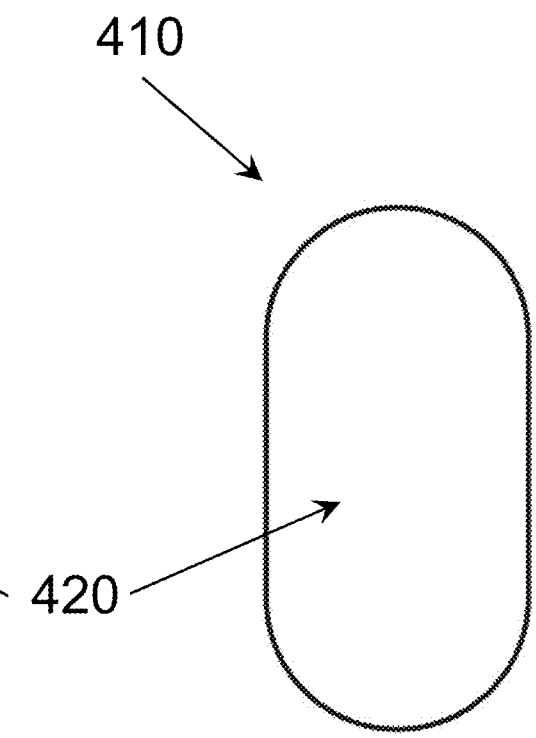
FIG. 21 is a side elevational view of the device of FIG. 20.
Figure 22:
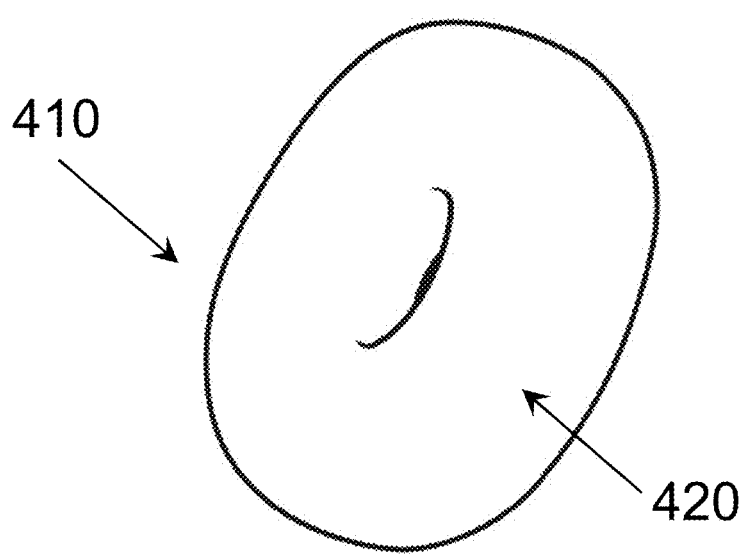
FIG. 22 is a perspective view of the device of FIG. 20.

Referring to FIGS. 20-22, there is shown another embodiment of a device 410 for alleviating dyspareunia constructed in accordance with principles of the present disclosure. In the embodiment illustrated in FIGS. 20-22, the device 410 includes a body 420. The illustrated body 420 is annular or ring-shaped. In use, a central hole 429 defined by the annular body 320 can be configured to accommodate at least one finger therethrough to help provide a grasping point for use during the removal of the device 410 from a user's vagina. As such, a retrieval strap can be omitted. The device 410 illustrated in FIGS. 20-22 does not include a retrieval strap mounted to the body 420. The construction and/or use of the device 410 of FIGS. 20-22 can be similar in other respects to the device 10 of FIGS. 1-6, the device 110 of FIGS. 8-12, the device of FIGS. 13-16, and/or the device 310 of FIGS. 17-19.

Figure 23:
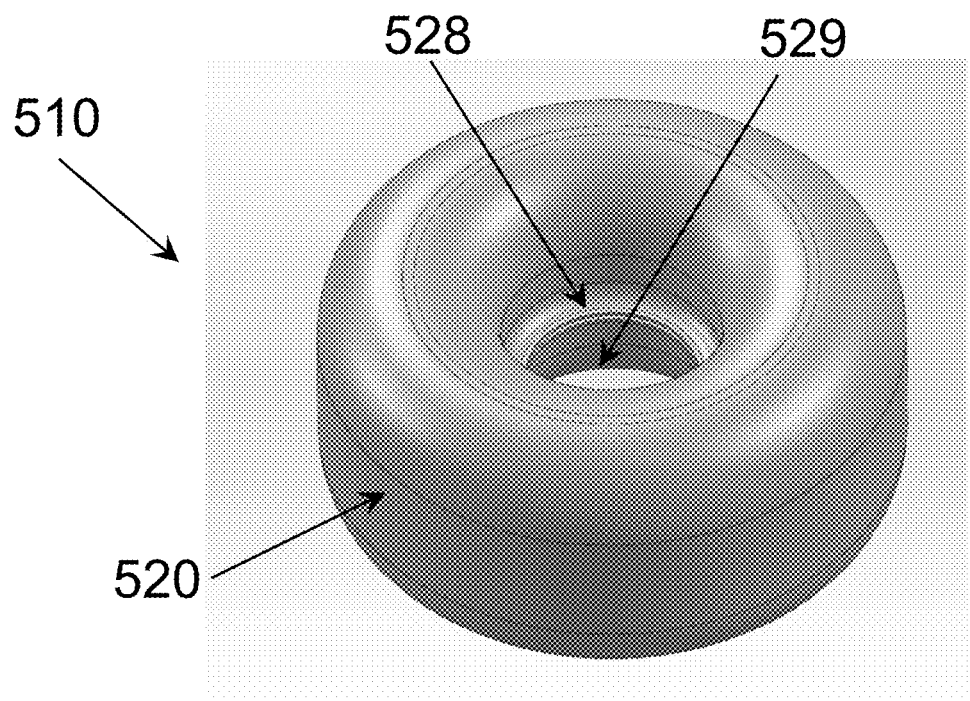
FIG. 23 is a perspective view of yet another embodiment of a device for alleviating dyspareunia constructed in accordance with principles of the present disclosure.
Figure 24:
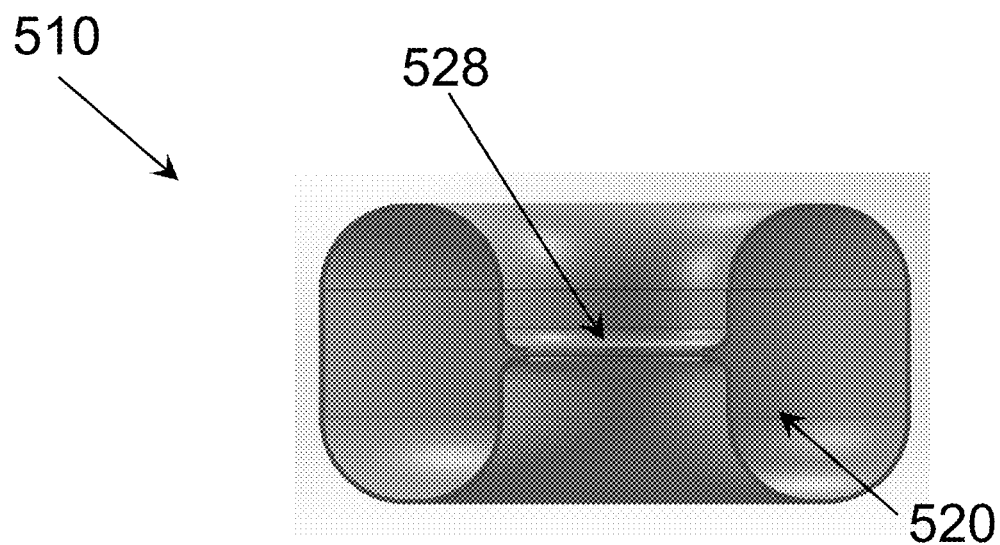
FIG. 24 is a sectional view of the device of FIG. 23.

Referring to FIGS. 23 and 24, there is shown another embodiment of a device 510 for alleviating dyspareunia constructed in accordance with principles of the present disclosure. In the embodiment illustrated in FIGS. 23 and 24, the device 510 includes a body 420. The illustrated body 520 is annular or ring-shaped. In use, the annular body 420 includes a central flange 528 that defines a central hole 529. The central hole 529 can be configured to accommodate at least one finger therethrough to help provide a grasping point for use during the removal of the device 510 from a user's vagina. As such, a retrieval strap can be omitted. The device 510 illustrated in FIGS. 23 and 24 does not include a retrieval strap mounted to the body 520. The construction and/or use of the device 510 of FIGS. 23 and 24 can be similar in other respects to the device 10 of FIGS. 1-6, the device 110 of FIGS. 8-12, the device of FIGS. 13-16, the device 310 of FIGS. 17-19, and/or the device 410 of FIGS. 20-22.

Figure 25:
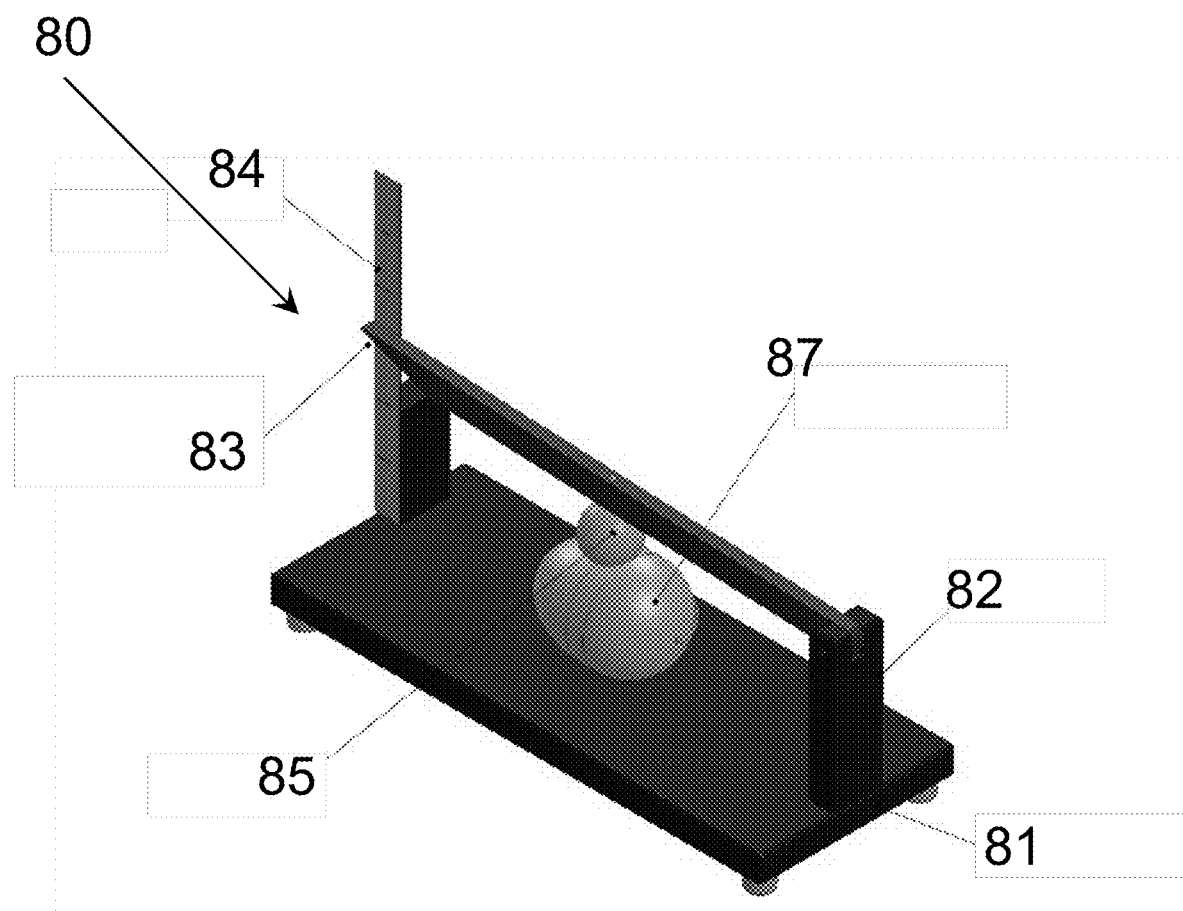
FIG. 25 is a perspective view of a resilience rebound test fixture suitable for use in evaluating a device for alleviating dyspareunia constructed in accordance with principles of the present disclosure, illustrating a device specimen installed in the test fixture for evaluation.

Referring to FIG. 25, there is shown a resilience rebound test fixture 80 suitable for use in evaluating a device 87 for alleviating dyspareunia constructed in accordance with principles of the present disclosure. The test fixture 80 includes a base 81, a fulcrum 82, a rebound test arm 83, a scale 84, and a ball 85. The base 81 supports the fulcrum 82 and the scale 84 with the fulcrum 82 and the scale 84 being disposed adjacent opposing ends of the base 81. The rebound test arm 83 is a known length (ten inches) and is pivotally connected at one end to an upper end of the fulcrum 82 such that the rebound test arm 83 can pivotally move over a predetermined range of travel. The range of movement of the rebound test arm 83 can be measured according to the movement of the opposing second end of the arm 83 along the scale 84. The scale 84 can be configured such that it displays a length of any suitable unit of measurement (e.g., centimeters or inches). The ball 85 can be constructed from polytetrafluoroethylene (PTFE), commercially available under the tradename Teflon®.

The test fixture 80 of FIG. 21 can be used to quantify the resilience or rebound of a device constructed according to principles of the present disclosure. In embodiments, a device 87 for alleviating dyspareunia constructed in accordance with principles of the present disclosure includes a body that is configured to provide a controlled amount of damping or energy absorption during impact. The test fixture 80 of FIG. 21 can be used to quantify the resilience or rebound of the body of a device 87 for alleviating dyspareunia constructed in accordance with principles of the present disclosure.

For the purpose of this "rebound test," the time required for the body of the device 87 mounted in the test fixture 80 of FIG. 21 to return to its original condition after being subjected to a known deflection (e.g., 0.5 inches) is measured. In one embodiment, to perform the rebound test, a specimen of a device 87 for alleviating dyspareunia constructed in accordance with principles of the present disclosure is manufactured and installed in the test fixture as shown in FIG. 21 with the ball 85 disposed between the device 87 and the rebound test arm 83. The resting position of the rebound test arm 83 along the scale 84 is noted, and the rebound test arm 83 is moved downwardly a predetermined amount (0.5 inches) as measured by the distal tip end of the rebound test arm 83 along the scale. The rebound test arm 83 is released, and the amount of time (seconds) for the rebound test arm 83 to return to the original resting position is measured.

In embodiments, a device for alleviating dyspareunia constructed in accordance with principles of the present disclosure has a rebound rate, as measured using the "rebound test" described above, of at least 2 seconds. In other embodiments, a device for alleviating dyspareunia constructed in accordance with principles of the present disclosure has a rebound rate, as measured using the "rebound test" described above, of at least 2.5 seconds. In yet other embodiments, a device for alleviating dyspareunia constructed in accordance with principles of the present disclosure has a rebound rate, as measured using the "rebound test" described above, of at least 2.75 seconds. In still other embodiments, a device for alleviating dyspareunia constructed in accordance with principles of the present disclosure has a rebound rate, as measured using the "rebound test" described above, of at least 3 seconds.

Figure 26:
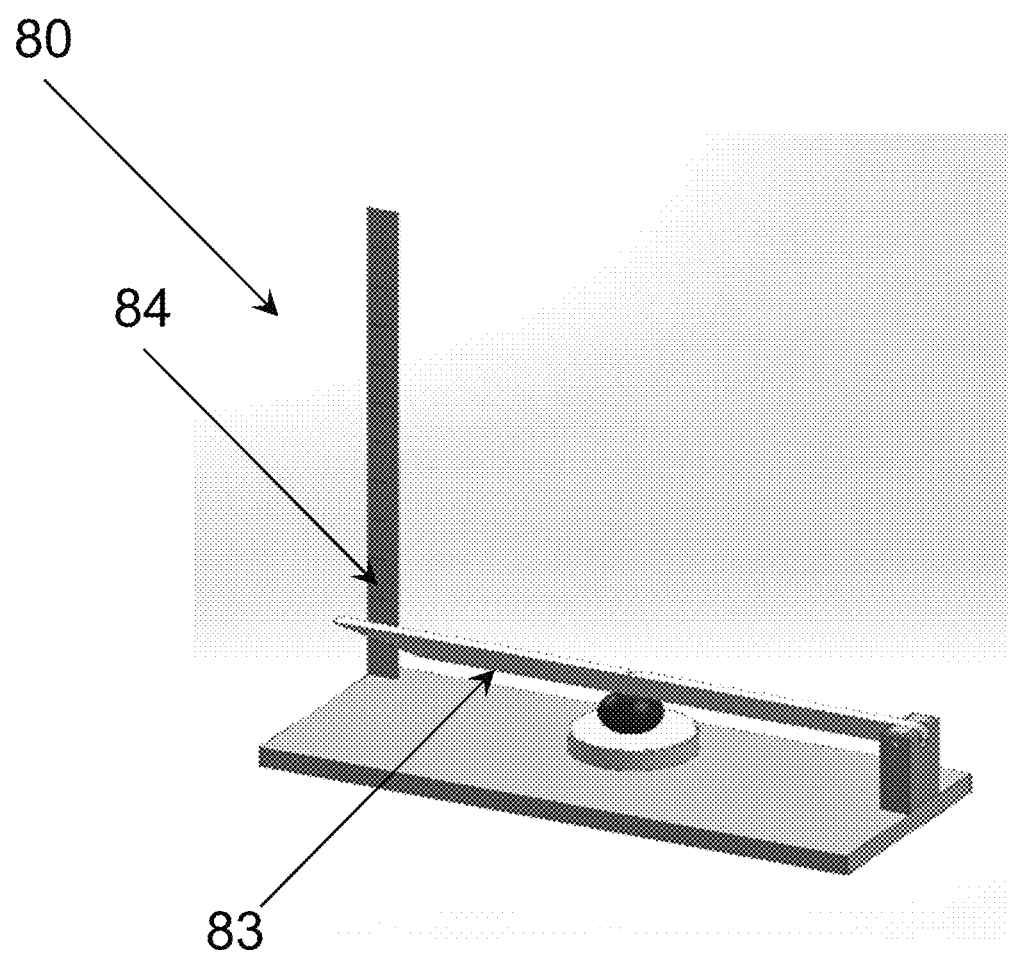
FIG. 26 is another perspective view of the test fixture of FIG. 25, illustrating a material sample installed in the test fixture for evaluation.

Referring to FIG. 26, the test fixture can also be used to evaluate a specimen of a core material composition comprising at least one material for use in a body of a device constructed according to principles of the present disclosure. In embodiments, the "rebound test" for a core material composition can be conducted on a specimen that is prepared by mixing 30 grams of the material in a plastic cup with two-inch diameter base (such as one commercially-available from McMaster-Carr, Model No. 41635T43). The material is allowed to cure as needed. Talc (e.g., cornstarch or baby powder) is applied to the top surface of the specimen of the core material composition in order to reduce any adhesive/sticking characteristics.

In one embodiment, to perform the rebound test, the specimen of the core material composition is manufactured as described above and is installed in the test fixture 80 as shown in FIG. 26. The resting position of the rebound test arm along the scale 84 is noted, and the rebound test arm is moved downwardly a predetermined amount (e.g., 0.5 inches) as measured by the distal tip end of the rebound test arm 83 along the scale 84. The rebound test arm 83 is released, and the amount of time (seconds) for the rebound test arm to return to the original resting position is measured.

In embodiments, a specimen of a core material composition for use in a body of a device constructed according to principles of the present disclosure has a rebound rate, as measured using the "rebound test" described above, of at least 2 seconds. In other embodiments, a specimen of a core material for use in a body of a device constructed according to principles of the present disclosure has a rebound rate, as measured using the "rebound test" described above, of at least 2.5 seconds. In still other embodiments, a specimen of a core material for use in a body of a device constructed according to principles of the present disclosure has a rebound rate, as measured using the "rebound test" described above, of at least 2.75 seconds. In yet other embodiments, a specimen of a core material for use in a body of a device constructed according to principles of the present disclosure has a rebound rate, as measured using the "rebound test" described above, of at least 3 seconds.

Figure 27:
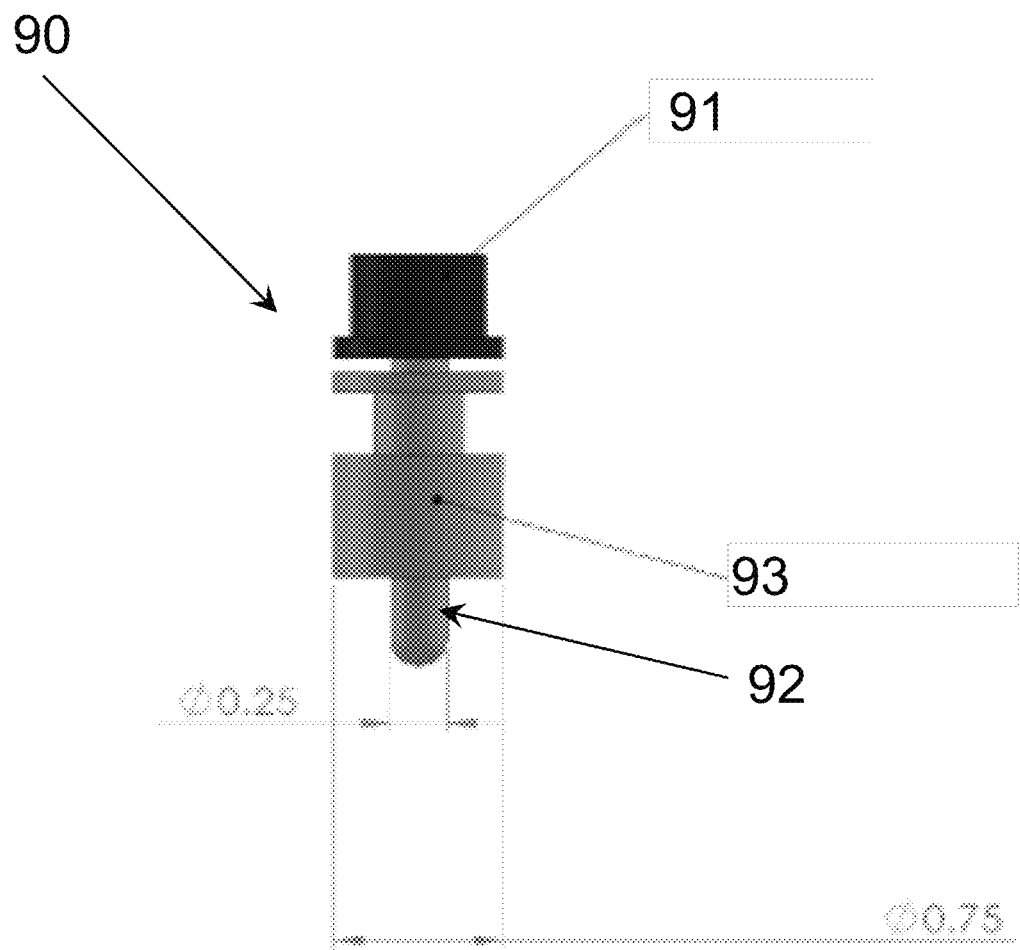
FIG. 27 is an elevational view of a penetrometer suitable for use in evaluating a device for alleviating dyspareunia constructed in accordance with principles of the present disclosure.

Referring to FIG. 27, there is shown a penetrometer 90 suitable for use in evaluating a device for alleviating dyspareunia constructed in accordance with principles of the present disclosure. The penetrometer 90 includes a cap mounted to a shaft 92 and a base 93 which slidingly receives the shaft 92 therein. The weight of the cap 91 and the shaft 92 together is 65.3 grams. There is a slip fit between the base 93 and the shaft 92 such that the shaft is movable with respect to the base 93.

Figure 28:
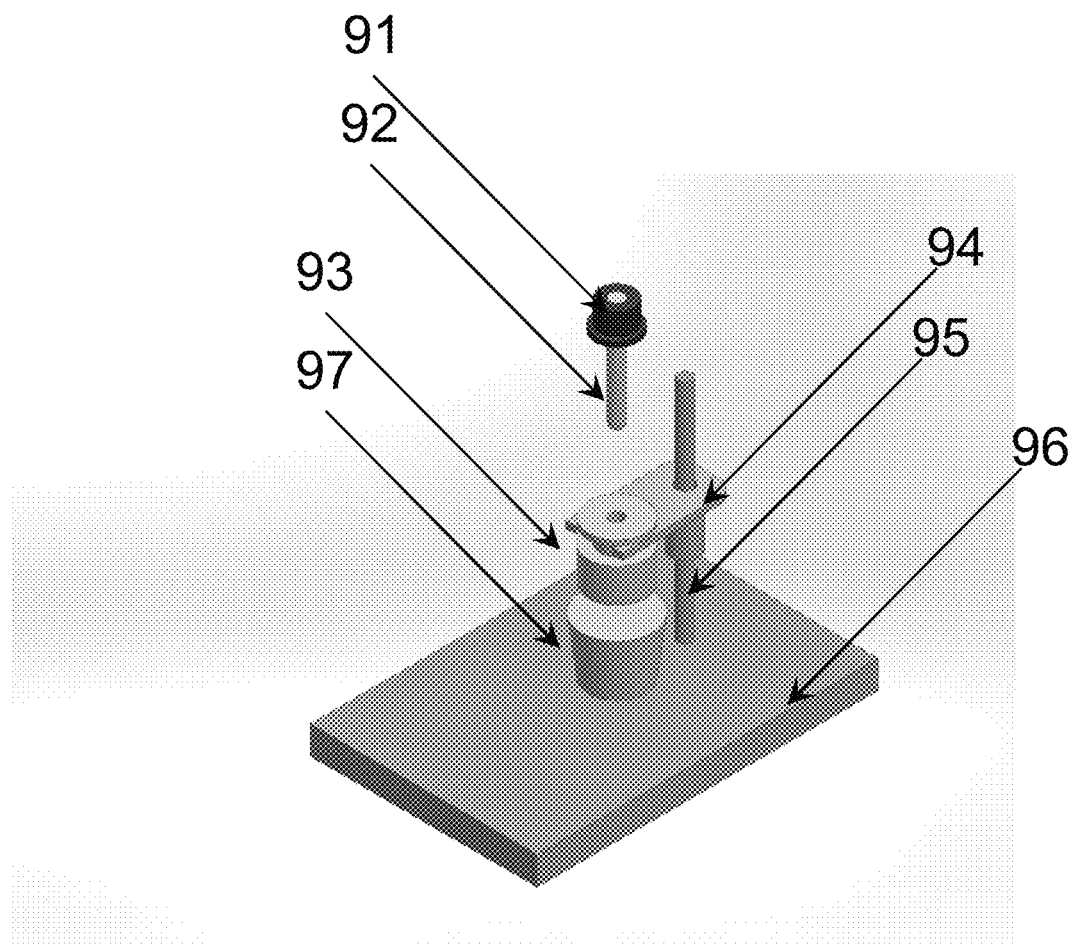
FIG. 28 is a perspective view of the penetrometer of FIG. 27 mounted to a holder for conducting a penetrometer test on a device for alleviating dyspareunia constructed in accordance with principles of the present disclosure.
Figure 29:
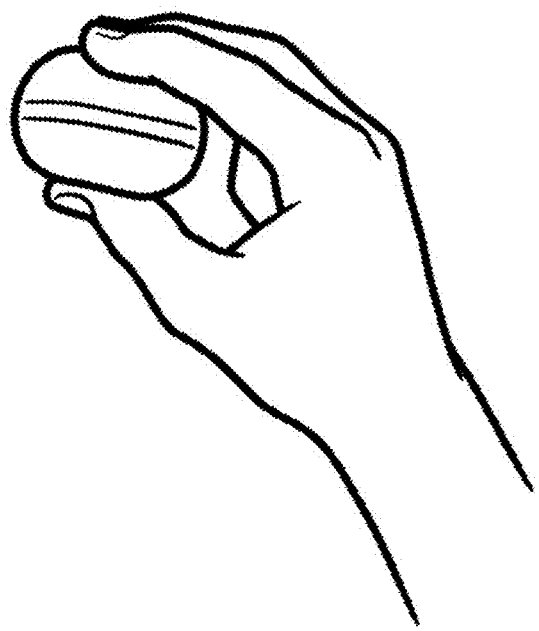
FIGS. 29-37 illustrate steps of an embodiment of a method of using a device for alleviating dyspareunia constructed in accordance with principles of the present disclosure.
Figure 30:
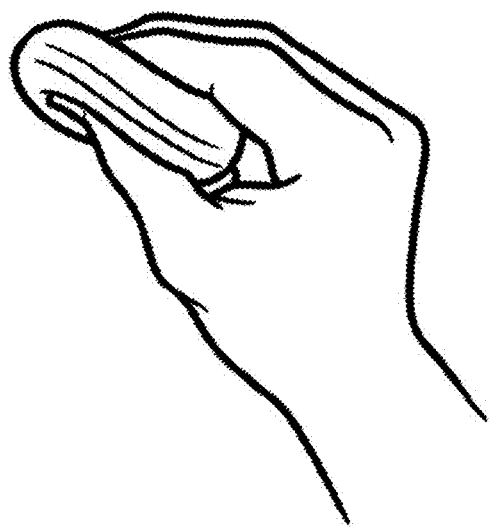
Figure 31:
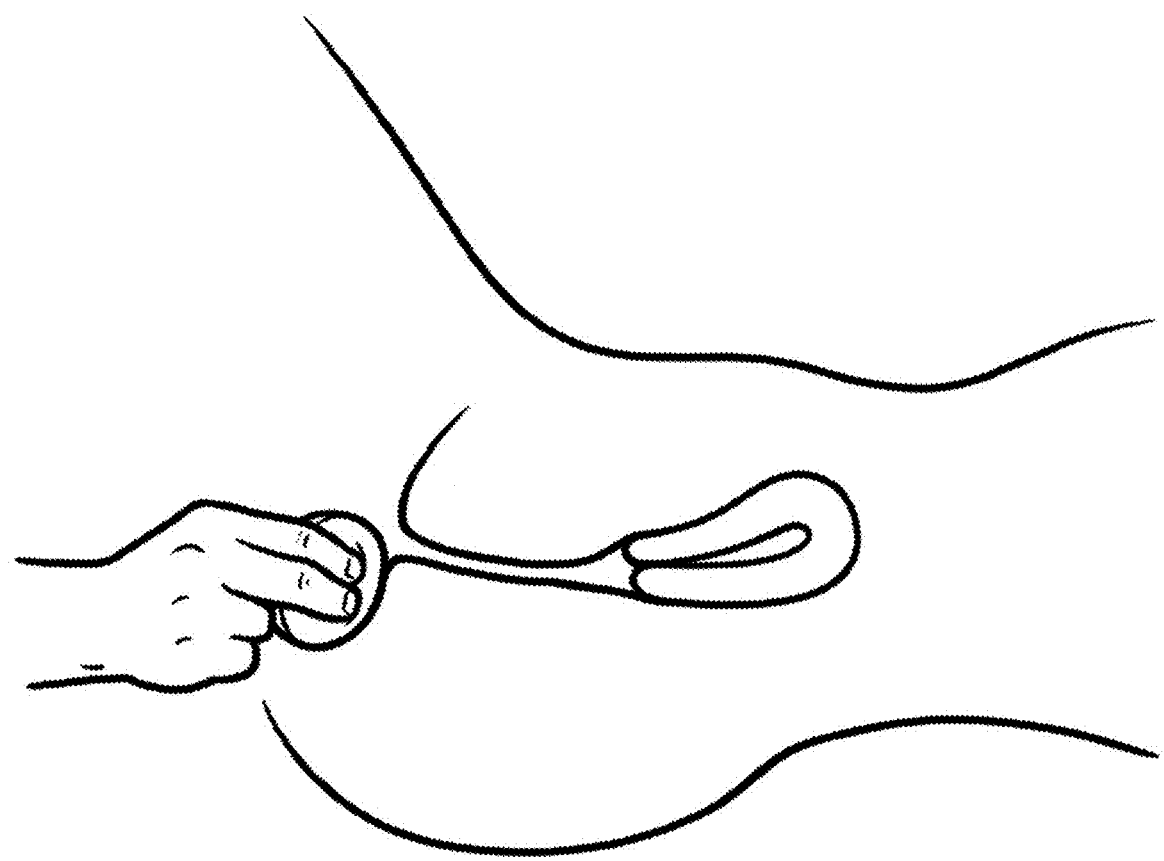
Figure 32:
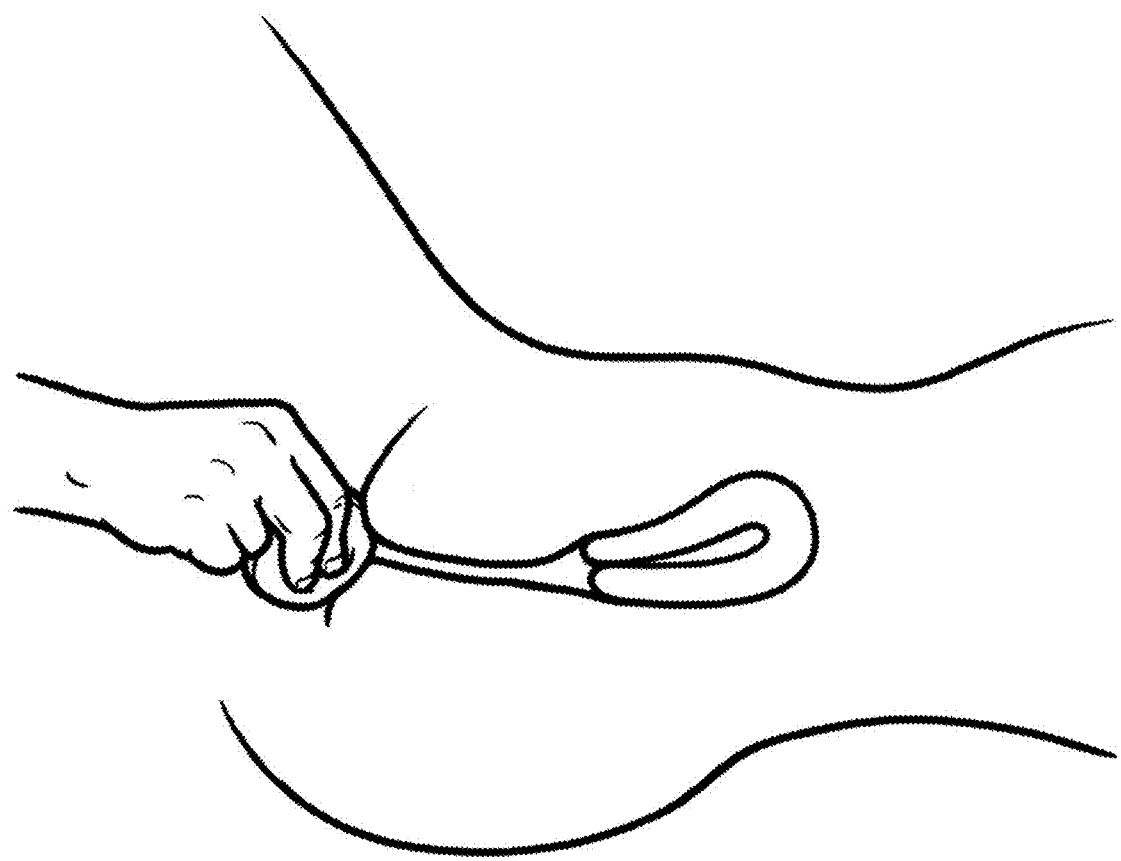
Figure 33:
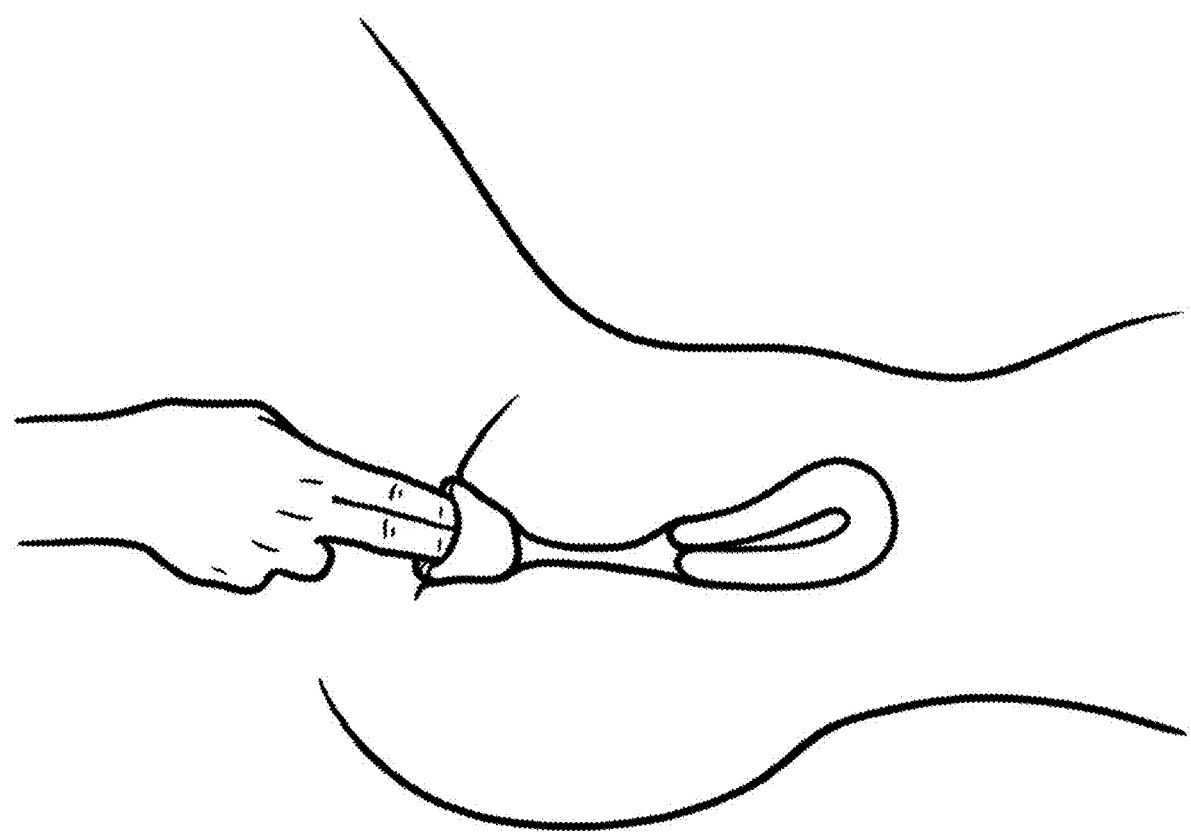
Figure 34:
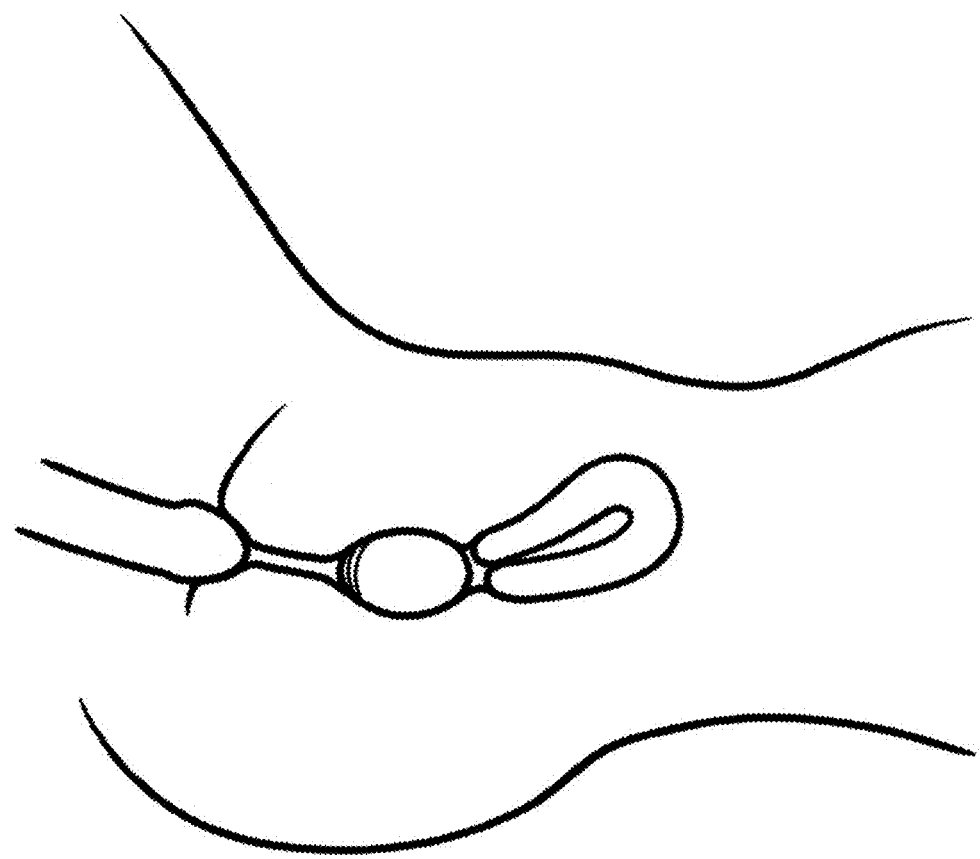
Figure 35:
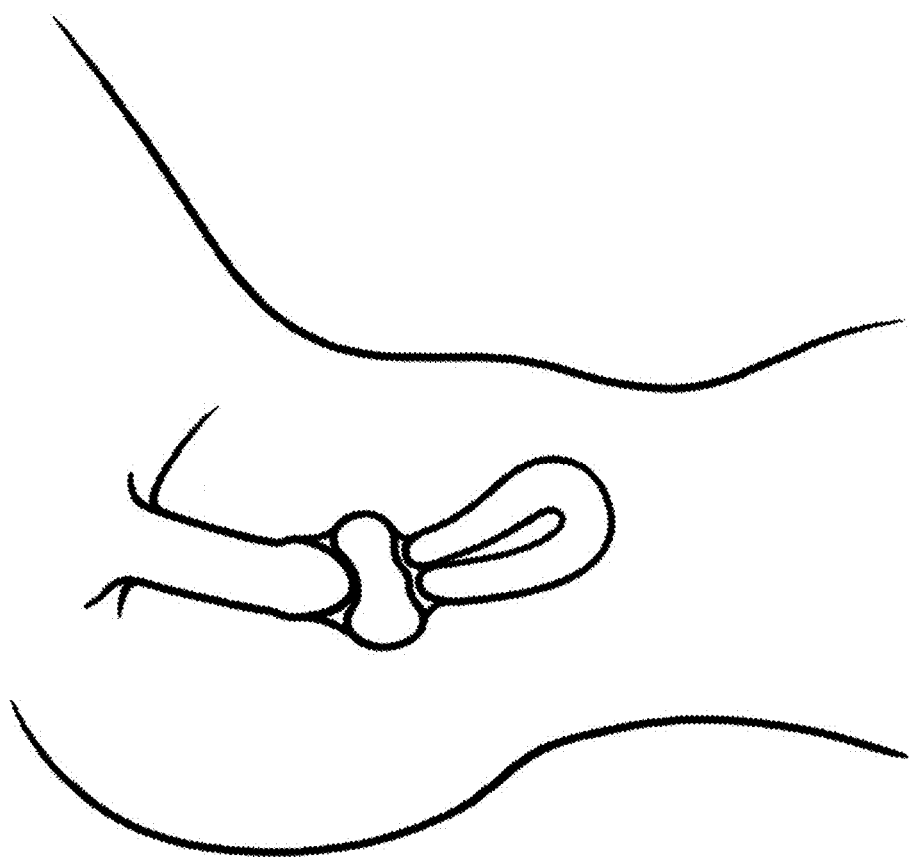
Figure 36:
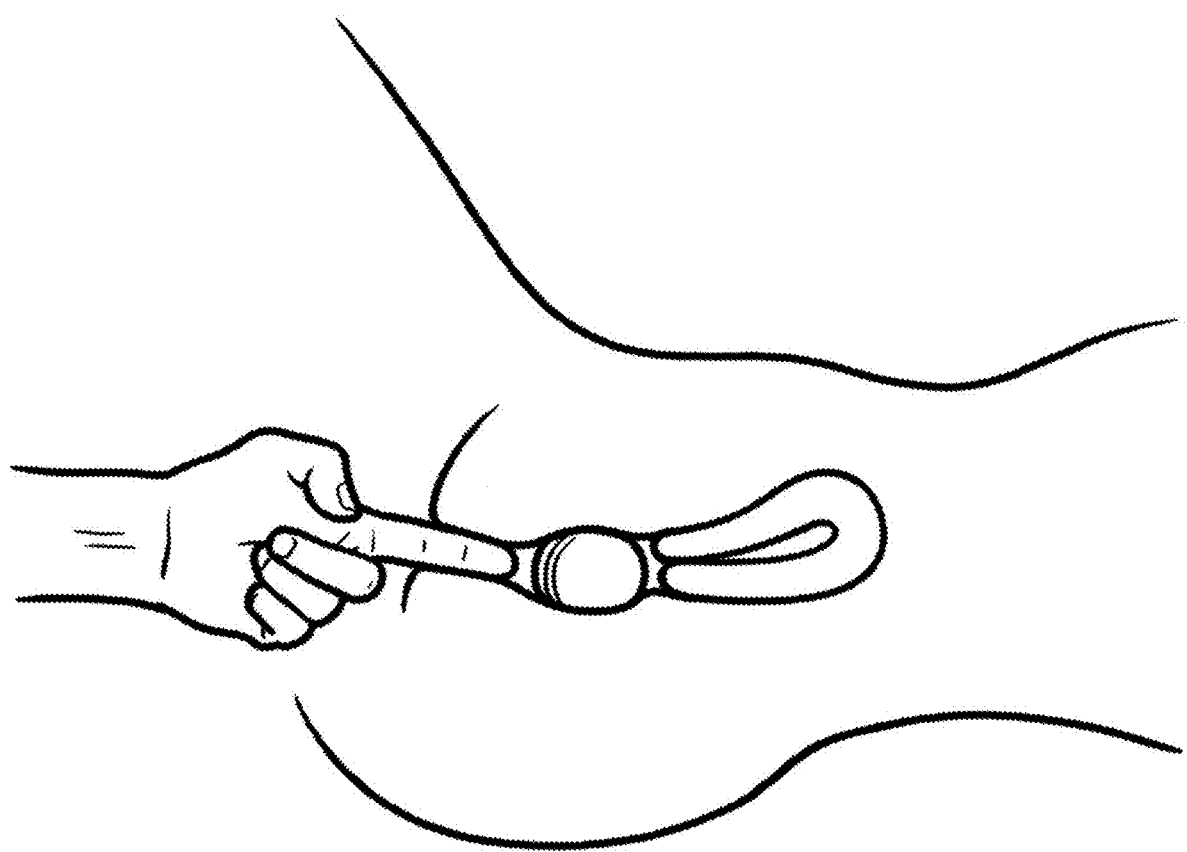
Figure 37:
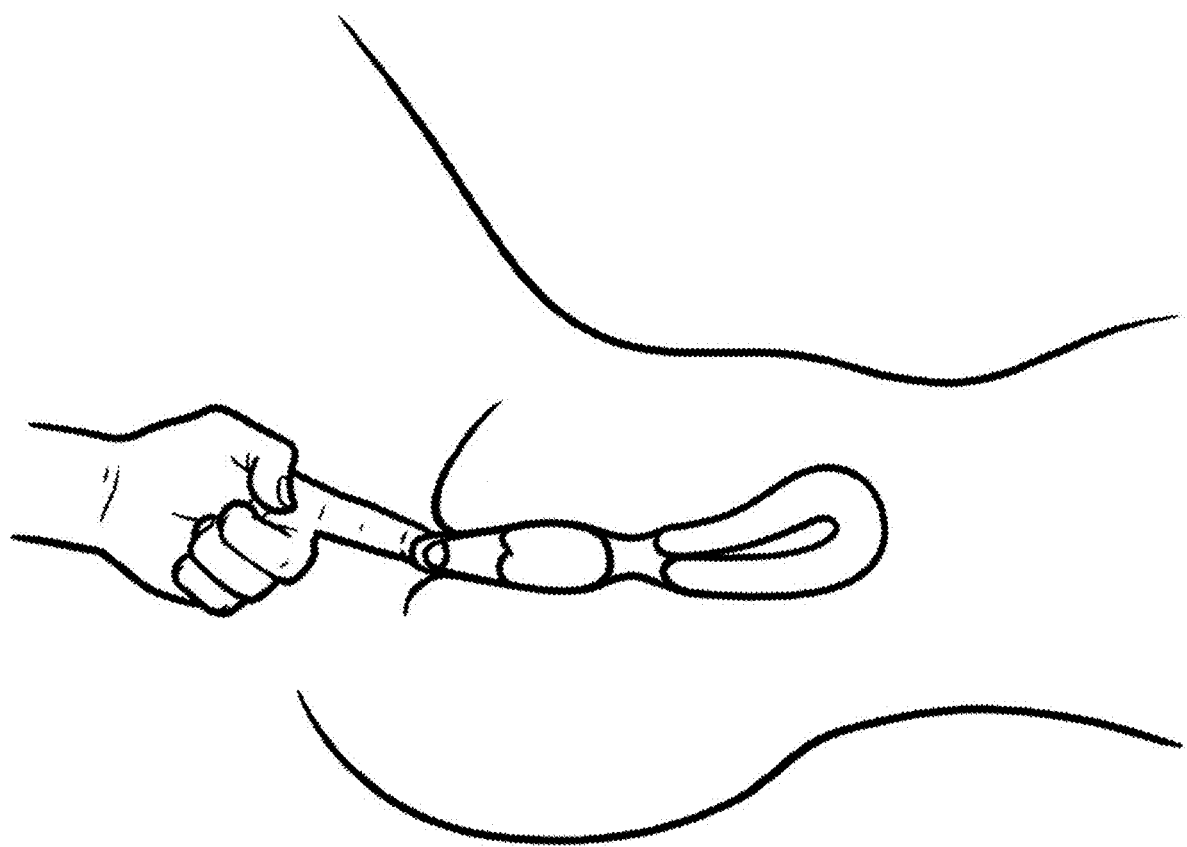
Figure 38:
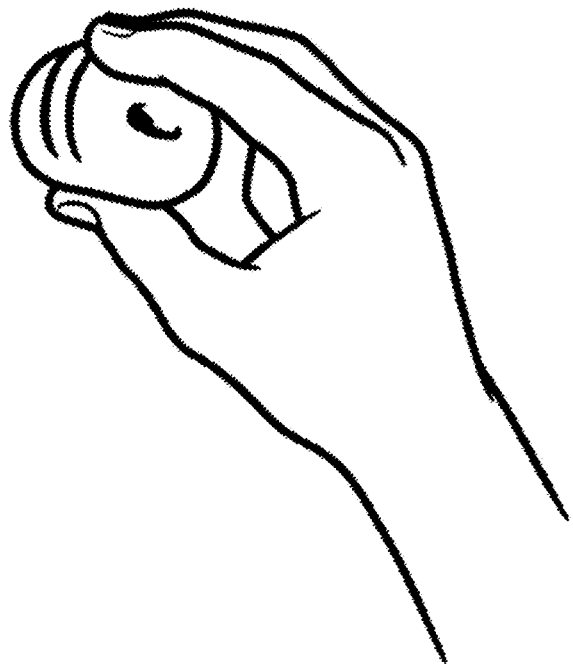
FIGS. 38-46 illustrate steps of an embodiment of a method of using another device for alleviating dyspareunia constructed in accordance with principles of the present disclosure.
Figure 39:
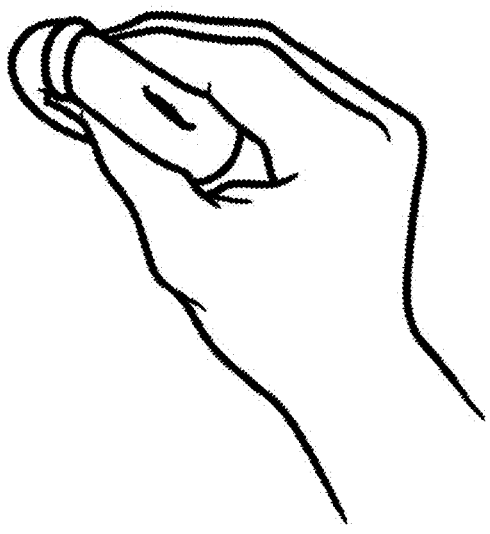
Figure 40:
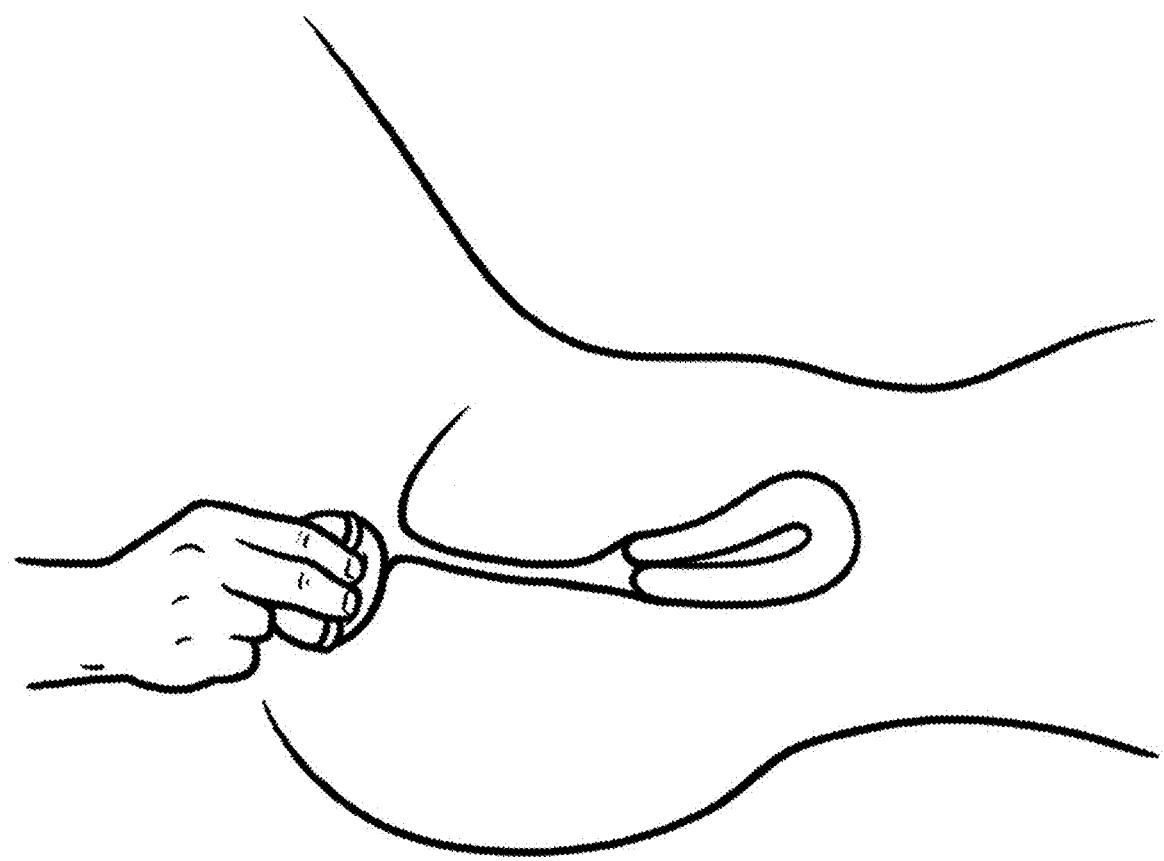
Figure 41:
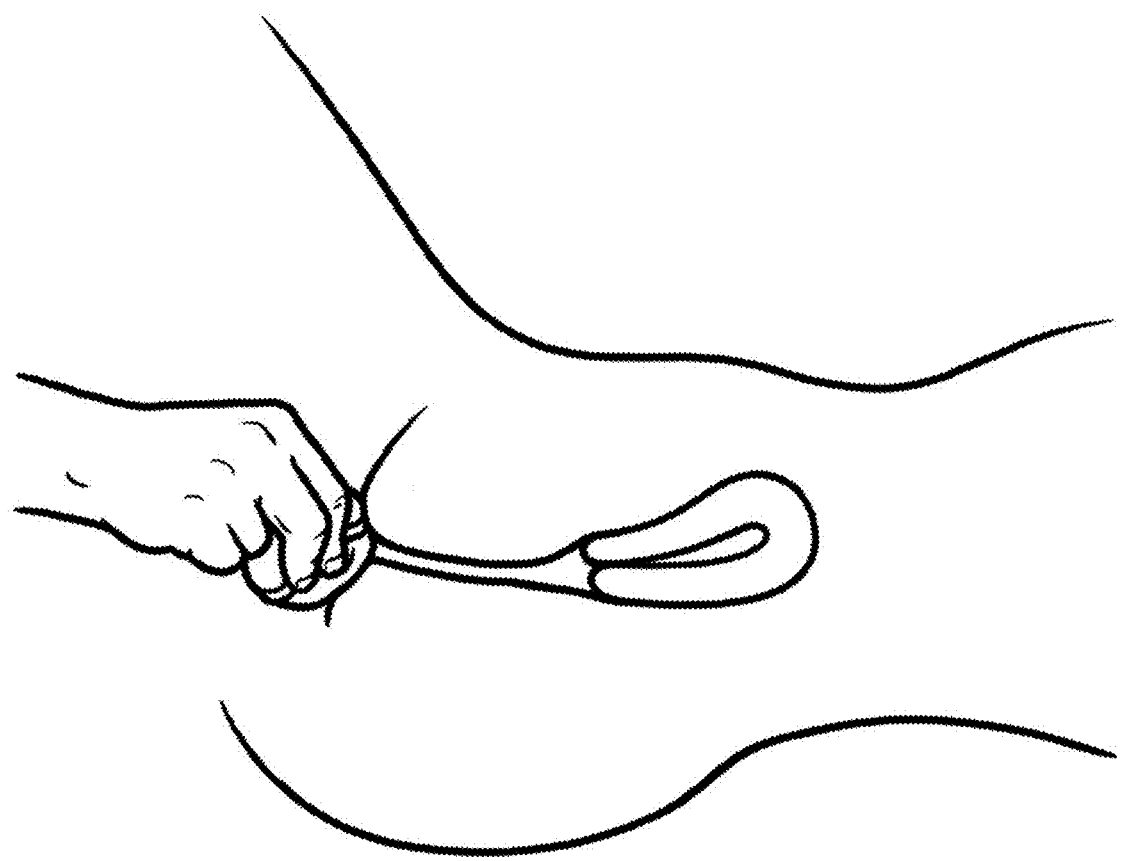
Figure 42:
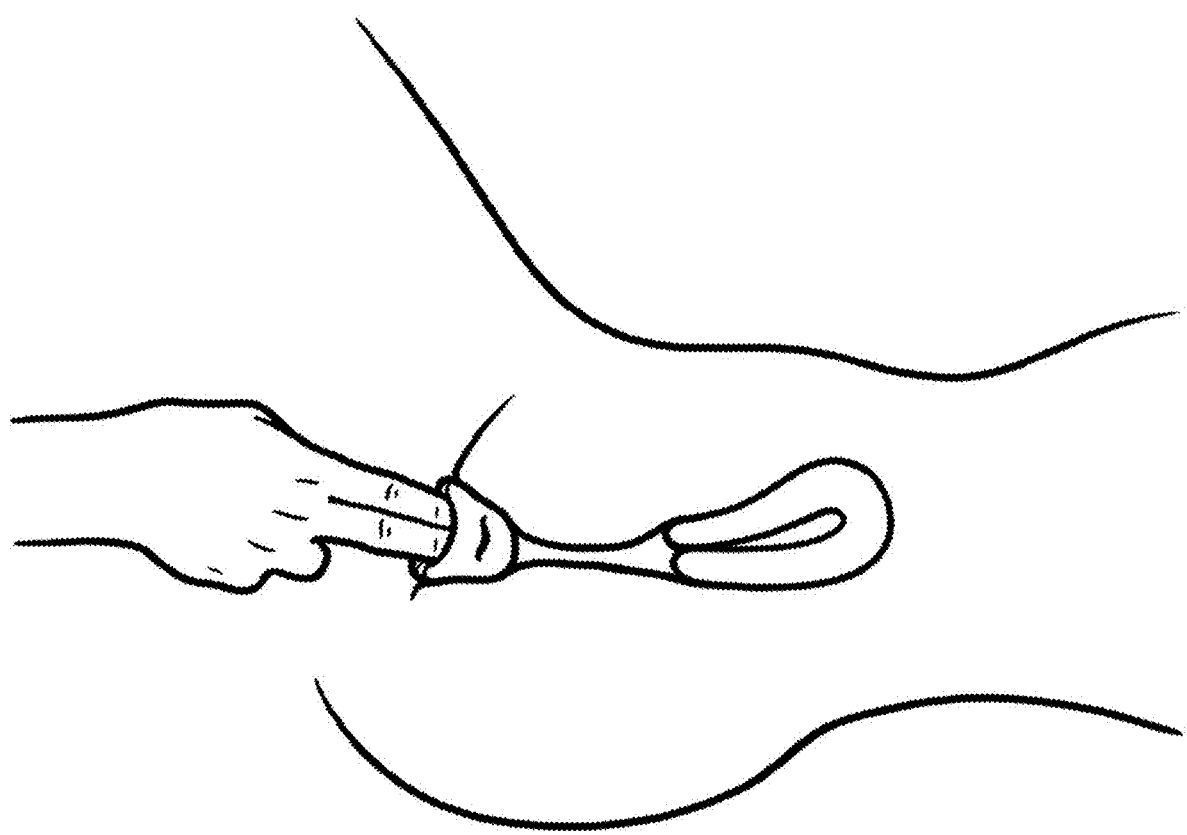
Figure 43:
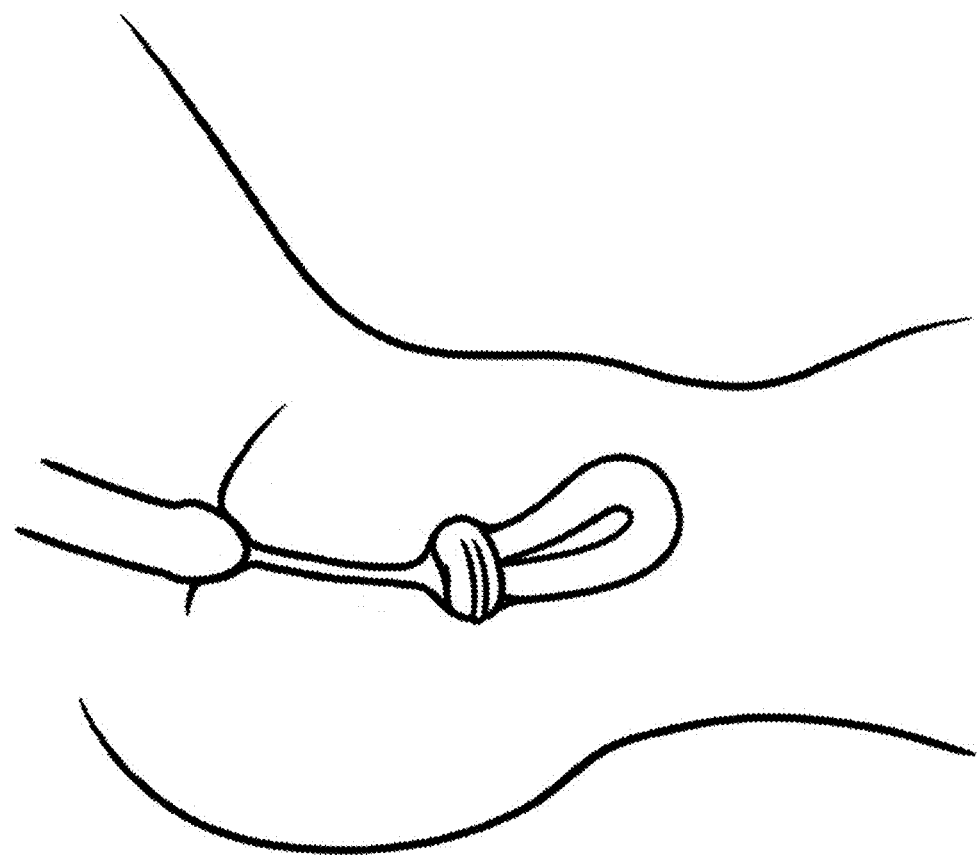
Figure 44:
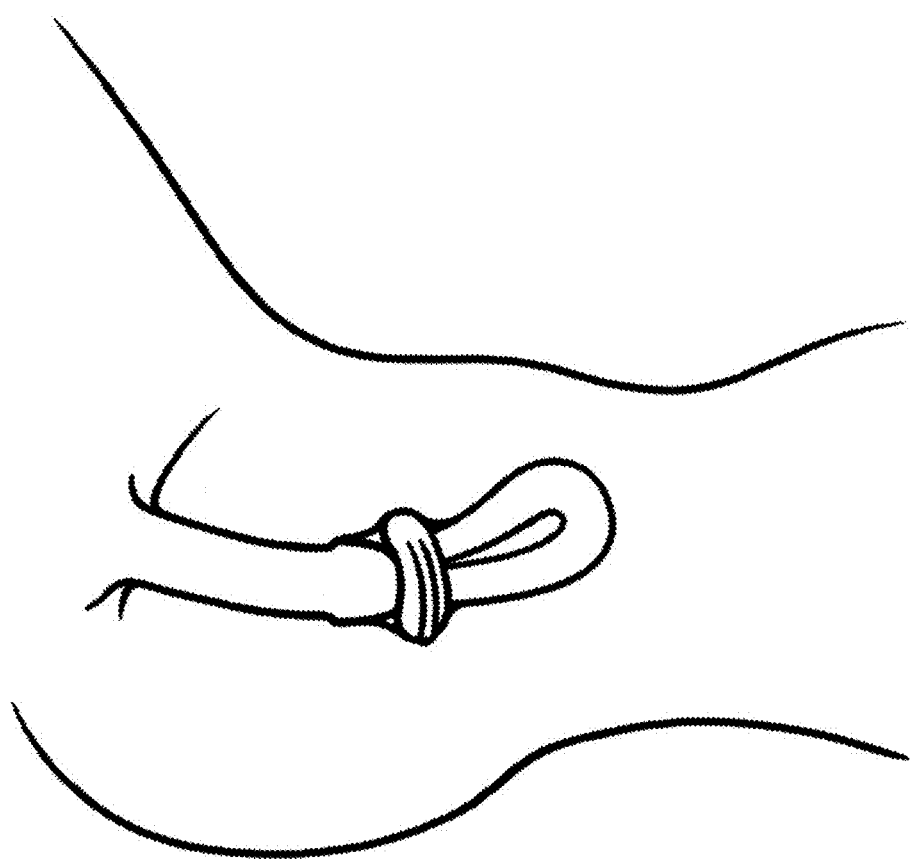
Figure 45:
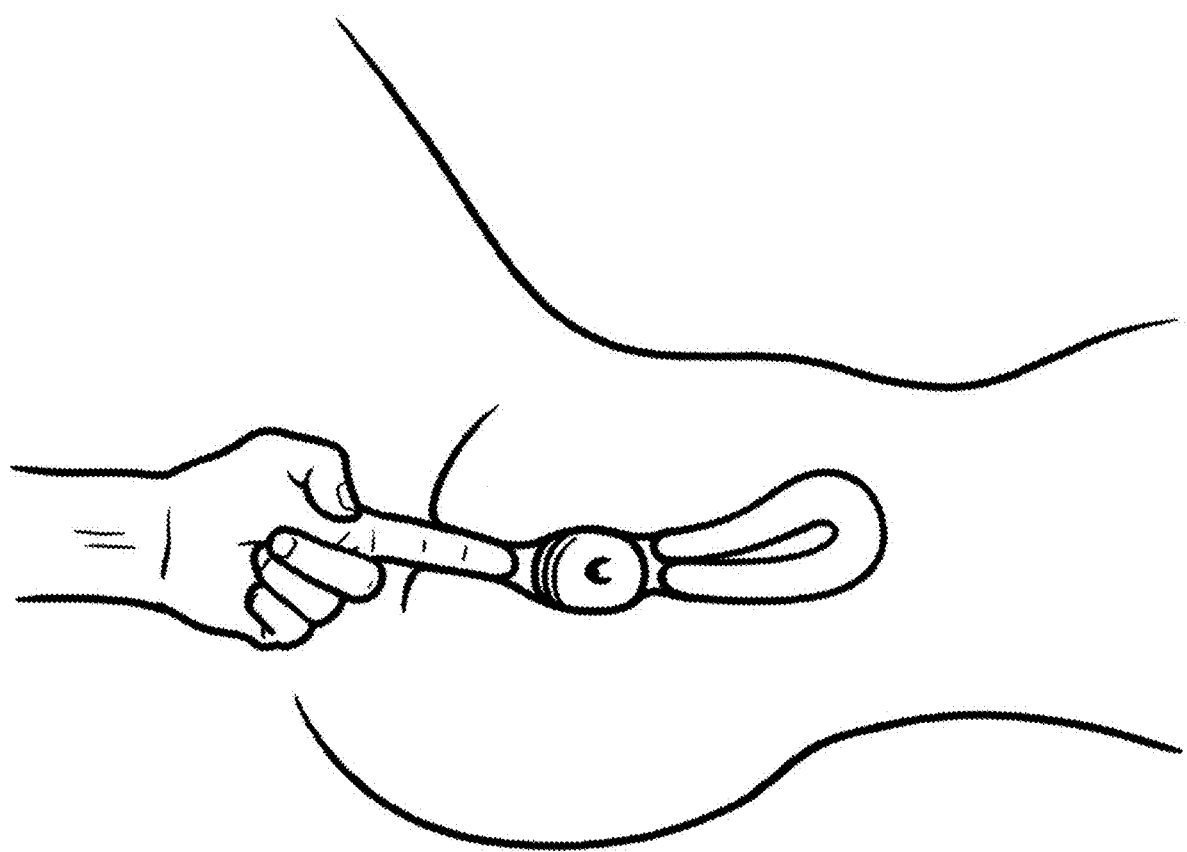
Figure 46:
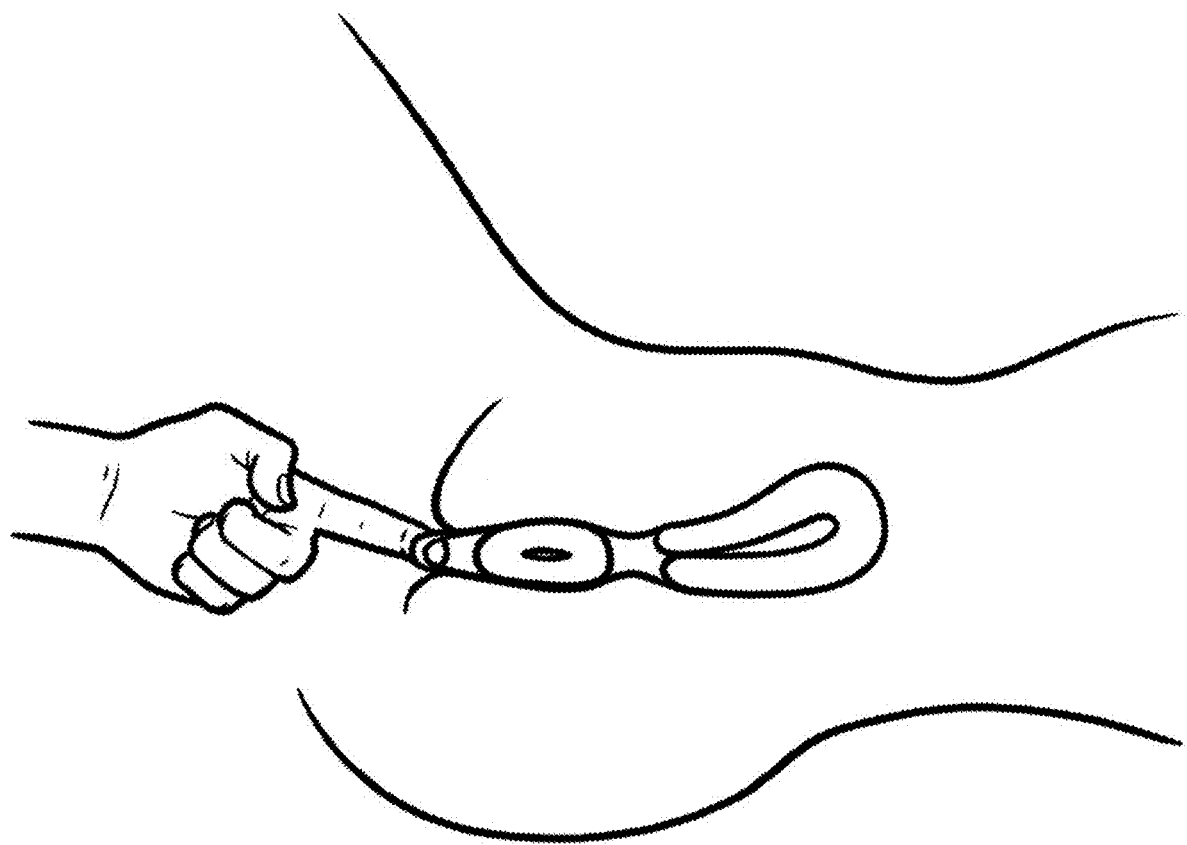

Referring to FIG. 28, the base 93 of the penetrometer 90 can be suspended upon a holder 94 which is slidably mounted to a post 95 secured to a base 96. The holder 94 can include a forked end which fits within a circumferential groove defined by the exterior surface of the base 96. A specimen 97 of a composition for a core can be placed upon the base 96 under the penetrometer 90. The holder 94 can be adjusted vertically along the post 95 to permit the bottom of the base 96 to engage the specimen 97 without deforming the specimen 97.

In embodiments, a device for alleviating dyspareunia constructed in accordance with principles of the present disclosure includes a body that is constructed to absorb energy during intercourse. The penetrometer of FIG. 23 can be used to evaluate the compliance of the body of the device under a given fixed load, which is understood to be correlated to positive clinical feedback.

For the purpose of a "penetrometer test," the deflection of the body of a device for alleviating dyspareunia constructed according to principles of the present disclosure in response to the application of a known load via the penetrometer 90 shown in FIG. 27 is measured. In one embodiment, to perform the penetrometer test, a specimen of the composition of the core of a device for alleviating dyspareunia constructed in accordance with principles of the present disclosure is manufactured and allowed to cure for at least one day. A light coat of talc is applied on the tester shaft 92. The penetrometer 90 of FIG. 27 is placed on the specimen such that the base 93 is contacting the specimen with the shaft 92 lifted up into the base 93 so that the distal tip of the shaft 92 is just in plane with the bottom of the base 93, but not deforming the specimen. The cap 91 and the shaft 92 are released to allow their weight (65.3 grams) to be applied against the specimen. The travel of the shaft is measured.

In embodiments, a device for alleviating dyspareunia constructed in accordance with principles of the present disclosure includes a body having a core made from a composition with a penetration amount, as measured using the "penetrometer test" described above, of at least 1 mm. In other embodiments, a device for alleviating dyspareunia constructed in accordance with principles of the present disclosure has a core made from a composition with a penetration amount, as measured using the "penetrometer test" described above, of at least 1.25 mm. In still other embodiments, a device for alleviating dyspareunia constructed in accordance with principles of the present disclosure has a core made from a composition with a penetration amount, as measured using the "penetrometer test" described above, of about 1.4 mm.

In embodiments, a device for alleviating dyspareunia constructed in accordance with principles of the present disclosure includes a body having a core made from a composition with a penetration amount, as measured using the "penetrometer test" described above, in a range between 1 mm and 2 mm. In other embodiments, a device for alleviating dyspareunia constructed in accordance with principles of the present disclosure includes a body having a core made from a composition with a penetration amount, as measured using the "penetrometer test" described above, in a range between 1.25 mm and 1.75 mm. In yet other embodiments, a device for alleviating dyspareunia constructed in accordance with principles of the present disclosure includes a body having a core made from a composition with a penetration amount, as measured using the "penetrometer test" described above, in a range between 1.25 mm and 1.5 mm.

For the purpose of a "penetrometer time test," the amount of time it takes for the deflection of the body of a device for alleviating dyspareunia constructed according to principles of the present disclosure in response to the application of a known load via the penetrometer 90 shown in FIG. 27 is measured. In one embodiment, to perform the penetrometer time test, a specimen of the composition of the core of a device for alleviating dyspareunia constructed in accordance with principles of the present disclosure is manufactured and allowed to cure for at least one day. A light coat of talc is applied on the tester shaft 92. The penetrometer 90 of FIG. 27 is placed on the specimen such that the base 93 is contacting the specimen with the shaft 92 lifted up into the base 93 so that the distal tip of the shaft 92 is just in plane with the bottom of the base 93, but not deforming the specimen. The cap 91 and the shaft 92 are controlled to apply a fixed load (foot force of 28.7 grams) to be applied against the specimen. The amount of time it takes for the shaft 92 to travel one-half inch is measured.

In embodiments, a device for alleviating dyspareunia constructed in accordance with principles of the present disclosure includes a body having a core made from a composition with a penetration time, as measured using the "penetrometer time test" described above, of at least three second. In other embodiments, a device for alleviating dyspareunia constructed in accordance with principles of the present disclosure has a core made from a composition with a penetration time, as measured using the "penetrometer time test" described above, of at least five seconds. In other embodiments, a device for alleviating dyspareunia constructed in accordance with principles of the present disclosure has a core made from a composition with a penetration time, as measured using the "penetrometer time test" described above, of at least seven seconds.

In embodiments, a device for alleviating dyspareunia constructed in accordance with principles of the present disclosure includes a body having a core made from a composition with a penetration time, as measured using the "penetrometer time test" described above, in a range between three seconds and twenty seconds. In other embodiments, a device for alleviating dyspareunia constructed in accordance with principles of the present disclosure includes a body having a core made from a composition with a penetration time, as measured using the "penetrometer time test" described above, in a range between five seconds and twenty seconds. In still other embodiments, a device for alleviating dyspareunia constructed in accordance with principles of the present disclosure includes a body having a core made from a composition with a penetration time, as measured using the "penetrometer time test" described above, in a range between three seconds and sixteen seconds.

Embodiments of a device for alleviating dyspareunia constructed according to principles of the present disclosure can be used to carry out a method of alleviating dyspareunia. In embodiments, a method of alleviating dyspareunia following principles of the present disclosure can be used with any embodiment of a device for alleviating dyspareunia according to principles discussed herein. For example, FIGS. 28-37 illustrate steps 710-790 of a method of alleviating dyspareunia following principles of the present disclosure using a device 110 constructed in a manner similar to that shown in FIGS. 8-10. FIGS. 38-46 illustrate steps 810-890 of another method of alleviating dyspareunia following principles of the present disclosure using a device 310 constructed in a manner similar to that shown in FIGS. 17-19.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A device for alleviating dyspareunia, the device comprising:
   a body, the body including an outer skin and a core disposed within the outer skin;
   a strap, the strap being connected to the body;
   wherein the outer skin of the body is made from a first composition including a first material, and the core of the body is made from a second composition comprising a second material, the first composition being harder than the second composition, and wherein the outer skin and the core are configured such that the body has a modulus of elasticity in a range between 5 kPa and 10 kPa.

2. The device for alleviating dyspareunia according to claim 1, wherein the body is ovoid.

3. The device for alleviating dyspareunia according to claim 2, wherein the body extends from a first end to a second end over a length, and the body has a maximum diameter in a plane transverse to its length, a ratio of the length to the maximum diameter being in a range between 1 and 1.5.

4. The device for alleviating dyspareunia according to claim 3, wherein the ratio of the length to the maximum diameter is in a range between 1.25 and 1.4.

5. The device for alleviating dyspareunia according to claim 1, wherein the body is annular.

6. The device for alleviating dyspareunia according to claim 1, wherein the body is configured to provide a controlled amount of energy absorption during impact.

7. The device for alleviating dyspareunia according to claim 1, wherein the second composition of the core has a penetration amount, as measured using the "penetrometer test," in a range between 1 mm and 2 mm.

8. The device for alleviating dyspareunia according to claim 1, wherein the second composition of the core has a penetration amount, as measured using the "penetrometer test," of at least 1.25 mm.

9. The device for alleviating dyspareunia according to claim 1, wherein the first material comprises an elastomeric material that has a hardness in a range from 10 to 40 Shore A.

10. The device for alleviating dyspareunia according to claim 9, wherein the second material comprises an elastomeric material that has a hardness in a range from 10 Shore 00 to 10 Shore A.

11. The device for alleviating dyspareunia according to claim 1, wherein the first material comprises silicone and the second material comprises silicone, the second material being different from the first material with respect to at least one property parameter.

12. The device for alleviating dyspareunia according to claim 1, wherein the second composition has a rebound rate, as measured using the "rebound test," of at least 2 seconds.

13. The device for alleviating dyspareunia according to claim 1, wherein the second composition has a rebound rate, as measured using the "rebound test," of at least 3 seconds.

14. The device for alleviating dyspareunia according to claim 1, wherein the strap is made from an elastomeric material that has a hardness greater than the hardness of the first composition and the second composition.

15. The device for alleviating dyspareunia according to claim 1, wherein the strap is made from an elastomeric material that has a hardness in a range from 10 to 40 Shore A.

16. The device for alleviating dyspareunia according to claim 1, wherein the strap is made from an elastomeric material, the strap is elongated and has a first end and a second end, the first end and the second end connected to the body at a first point and a second point, respectively, the first point being discontinuous from the second point, and the strap has an intermediate portion disposed between the first and second ends, the intermediate portion of the strap not connected to the body such that the intermediate portion provides a finger loop that can be grasped in order to facilitate the removal of the device from a user's vagina.

17. The device for alleviating dyspareunia according to claim 16, wherein the body is ovoid and includes opposing first and second ends, the body extending from the first end to a second end, and wherein the first and second ends of the strap are respectively mounted to the first and second ends of the body.

18. The device for alleviating dyspareunia according to claim 16, wherein the first and second ends of the strap each includes a post projecting therefrom, and the device further comprising:
    a first mounting button and a second mounting button, each of the first and second mounting buttons defining a central opening therethrough, the first and second mounting buttons respectively mounted to the body at the first and second points thereof, the first mounting button interposed between the body and the first end of the strap such that the post projecting from the first end of the strap extends through the central opening of the first mounting button, and the second mounting button interposed between the body and the second end of the strap such that the post projecting from the second end of the strap extends through the central opening of the second mounting button.

19. The device for alleviating dyspareunia according to claim 16, wherein the body includes a central flange that defines the central hole.

20. A device for alleviating dyspareunia, the device comprising:
    a body, the body including an outer skin and an inner core disposed within the outer skin, the outer skin being made from a first composition including a first material, and the inner core being made from a second composition comprising a second material, the first composition being harder than the second composition;
    wherein the outer skin and the core are configured such that the body has a modulus of elasticity in a range between 5 kPa and 10 kPa;
    wherein the body is annular and defines a central hole, the central hole being configured to accommodate at least one finger therethrough for providing a grasping point for use during removal of the device from a user's vagina.

\* \* \* \* \*